US011173057B2

(12) United States Patent
Smith et al.

(10) Patent No.: US 11,173,057 B2
(45) Date of Patent: Nov. 16, 2021

(54) VOLUME ADJUSTABLE TRANSTIBIAL SOCKET

(71) Applicants: Andrew Smith, Tempe, AZ (US); Patrick Hogan, Tempe, AZ (US); Jeffrey LaBelle, Tempe, AZ (US)

(72) Inventors: Andrew Smith, Tempe, AZ (US); Patrick Hogan, Tempe, AZ (US); Jeffrey LaBelle, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 72 days.

(21) Appl. No.: 16/700,621

(22) Filed: Dec. 2, 2019

(65) Prior Publication Data

US 2020/0170811 A1 Jun. 4, 2020

Related U.S. Application Data

(60) Provisional application No. 62/773,341, filed on Nov. 30, 2018.

(51) Int. Cl.
*A61F 2/80* (2006.01)
*A61F 2/50* (2006.01)
*A61F 2/00* (2006.01)
*A61F 2/60* (2006.01)

(52) U.S. Cl.
CPC .............. *A61F 2/80* (2013.01); *A61F 2/0063* (2013.01); *A61F 2002/503* (2013.01); *A61F 2002/607* (2013.01)

(58) Field of Classification Search
CPC ........................................................ A61F 2/80
See application file for complete search history.

(56) References Cited

U.S. PATENT DOCUMENTS

| 6,289,558 B1 | 9/2001 | Hammerslag |
| 7,488,349 B2 | 2/2009 | Einarsson |
| 7,867,286 B2 | 1/2011 | Einarsson |

(Continued)

FOREIGN PATENT DOCUMENTS

| WO | 2014052470 A1 | 4/2014 |
| WO | 2015183893 A1 | 12/2015 |

(Continued)

OTHER PUBLICATIONS

U.S. Appl. No. 16/806,418, LaBelle et al., filed Mar. 2, 2020.

(Continued)

*Primary Examiner* — Jacqueline Woznicki
(74) *Attorney, Agent, or Firm* — Withrow & Terranova, P.L.L.C.

(57) ABSTRACT

A transtibial socket for a prosthetic lower limb includes a mesh arranged between rigid struts. The mesh includes a plurality of support members and a plurality of tensile members, optionally in combination with spacer members arranged between different support members. At least one tensioning member coupled with the tensile member extends through of past guides in the struts to an adjustable tensioning apparatus that is configured to allow the mesh to be constricted radially by the amputee-user. The mesh allows for the heat dissipation and volume adjustment, while increasing contact area and force distribution around a residual limb.

20 Claims, 22 Drawing Sheets

(56) References Cited

U.S. PATENT DOCUMENTS

| | | |
|---|---|---|
| 8,443,501 B2 | 5/2013 | Mahon |
| 9,909,942 B2 | 3/2018 | LaBelle et al. |
| 9,956,094 B2 | 5/2018 | Mahon |
| 9,962,273 B2 | 5/2018 | Bache et al. |
| 10,004,614 B1* | 6/2018 | Johnson .............. A61F 2/7812 |
| 10,172,728 B2 | 1/2019 | Hurley et al. |
| 10,219,918 B2 | 3/2019 | LaBelle et al. |
| 2003/0078674 A1* | 4/2003 | Phillips .............. A61F 2/7843 623/37 |
| 2003/0181990 A1* | 9/2003 | Phillips .............. A61F 2/80 623/37 |
| 2005/0288790 A1* | 12/2005 | Swords .............. A61F 2/2875 623/17.19 |
| 2007/0225824 A1* | 9/2007 | Einarsson .............. A61F 2/78 623/36 |
| 2007/0276510 A1* | 11/2007 | Becker .............. B29C 70/30 623/33 |
| 2009/0076625 A1* | 3/2009 | Groves .............. A61F 2/80 623/34 |
| 2012/0101597 A1 | 4/2012 | Bache |
| 2012/0289964 A1* | 11/2012 | Nakaji .............. A61B 17/688 606/80 |
| 2012/0330435 A1* | 12/2012 | Engqvist .............. A61L 31/026 623/23.61 |
| 2013/0053900 A1* | 2/2013 | Qwarnstrom ........ A61B 17/688 606/286 |
| 2013/0123940 A1 | 5/2013 | Hurley et al. |
| 2014/0005798 A1 | 1/2014 | Bache et al. |
| 2014/0277584 A1* | 9/2014 | Hurley .............. A61F 2/5044 623/33 |
| 2014/0379097 A1* | 12/2014 | Hurley .............. A61F 2/80 623/33 |
| 2015/0250624 A1* | 9/2015 | Mosler .............. A61F 2/80 623/36 |
| 2015/0268108 A1 | 9/2015 | LaBelle et al. |
| 2016/0074178 A1* | 3/2016 | Phillips .............. A61F 2/76 264/222 |
| 2016/0324666 A1* | 11/2016 | Barberio .............. A61F 5/0118 |
| 2017/0105853 A1* | 4/2017 | Jonsson .............. A61F 2/7812 |
| 2017/0202691 A1 | 7/2017 | LaBelle et al. |
| 2017/0239054 A1* | 8/2017 | Engstrand .............. A61B 17/688 |
| 2018/0036151 A1* | 2/2018 | Garus .............. A61F 2/7812 |
| 2018/0049897 A1 | 2/2018 | Lathers et al. |
| 2018/0098865 A1* | 4/2018 | Mojica .............. A61F 2/7812 |
| 2018/0153716 A1 | 6/2018 | Martin |
| 2018/0235779 A1* | 8/2018 | Dudding .............. A61F 2/80 |
| 2018/0243111 A1* | 8/2018 | Hand .............. A61F 2/5046 |
| 2018/0281340 A1* | 10/2018 | Brienza .............. B32B 3/06 |
| 2018/0296373 A1* | 10/2018 | Granz .............. A61F 2/60 |
| 2018/0303637 A1* | 10/2018 | Bache .............. A61F 2/66 |
| 2019/0000650 A1 | 1/2019 | Mahon |
| 2019/0053917 A1* | 2/2019 | Mosler .............. A61F 2/7812 |
| 2019/0054277 A1 | 2/2019 | LaBelle et al. |
| 2019/0091043 A1* | 3/2019 | Pawlik .............. A61F 2/80 |
| 2019/0160206 A1 | 5/2019 | Lathers et al. |
| 2019/0234816 A1 | 8/2019 | LaBelle et al. |
| 2019/0328315 A1 | 10/2019 | LaBelle et al. |
| 2020/0100920 A1* | 4/2020 | Finke .............. B33Y 70/00 |
| 2020/0170811 A1* | 6/2020 | Smith .............. A61F 2/5044 |
| 2020/0352748 A1* | 11/2020 | Dillingham .............. A61F 2/80 |
| 2020/0397602 A1* | 12/2020 | Martin .............. A61F 2/7843 |
| 2021/0038410 A1* | 2/2021 | Sampson .............. A61F 2/7812 |

FOREIGN PATENT DOCUMENTS

| | | |
|---|---|---|
| WO | 2016014572 A1 | 1/2016 |
| WO | 2017147041 A1 | 8/2017 |
| WO | 2018067626 A1 | 4/2018 |

OTHER PUBLICATIONS

Paternó, Linda, et al., "Sockets for Limb Prostheses: A Review of Existing Technologies and Open Challenges," IEEE Transactions on Biomedical Engineering, vol. 65, No. 9, Sep. 2018, pp. 1996-2010.

* cited by examiner

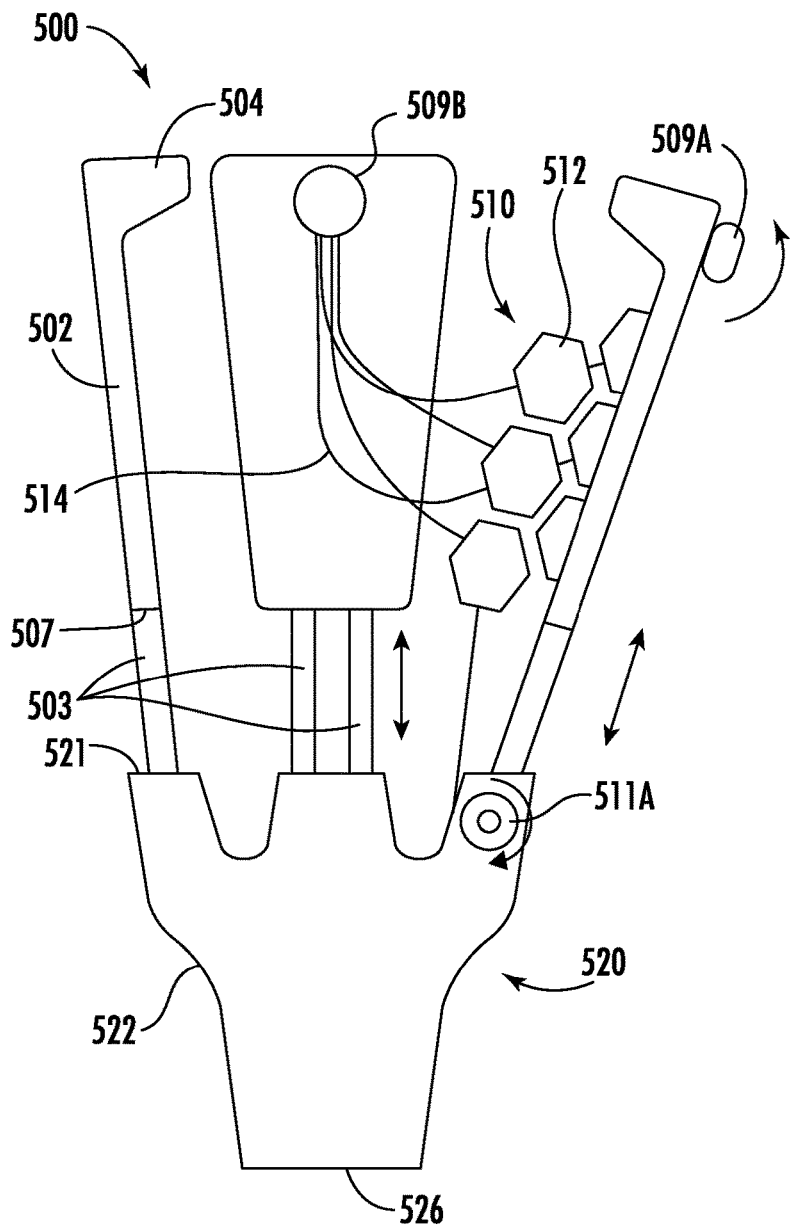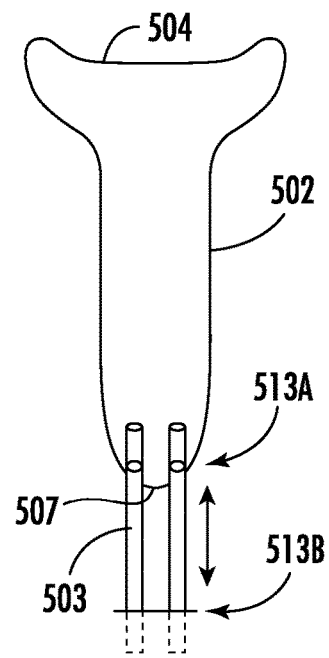
FIG. 21A
FIG. 21B

VOLUME ADJUSTABLE TRANSTIBIAL SOCKET

CROSS-REFERENCE TO RELATED APPLICATION(S)

This application claims benefit of U.S. Provisional Patent Application No. 62/773,341 filed on Nov. 30, 2018, wherein the disclosure of the foregoing application is hereby incorporated by reference as if set forth fully herein.

TECHNICAL FIELD

This disclosure relates to interfaces between a residual limb and prosthetic components, and more particularly to transtibial sockets for interfacing with prosthetic lower limbs, as well as methods for their manufacture and use.

BACKGROUND

In the United States, about two million people have lost a limb, with hospital costs for amputations of approximately $8.3 billion each year. It is estimated that the total number of lower limb amputees in the United Stated is about 1.46 million, with this number growing by about 185,000 per year. 54% of limb losses are attributable to vascular diseases, including diabetes and peripheral arterial disease; about 45% of limb losses are attributable to physical trauma; and fewer than 2% of limb losses are attributable to cancer, with a ratio of upper limb to lower limb loss of 1:4. Prosthetics can cost up to $50,000 per limb, and a significant number (possibly a majority) are not covered by insurance. Additionally, many prosthetics need to be replaced as the user grows, and health insurance frequently does not cover the cost of continual replacement.

One desirable focus of this disclosure will be on lower limb prosthetics and specifically transtibial (below-knee) sockets. Essential parts of prostheses are a socket and a suspension mechanism, as these parts provide a connection between the residual limb and device.

The most common sockets are pin-lock and suction-based designs that utilize a solid, custom formed outer shell, made to fit over a silicone liner rolled over the residual limb, and exhibit the highest level of force distribution over the residual limb. These sockets allow little airflow, heat dissipation, moisture wicking, and volume adjustment, which creates a stressful environment for the tissue of the residual limb. The snug fit of a prosthetic socket over a residual limb and lack of heat transfer out of a socket can disturb thermal balance, which results in moisture collection, loss of friction, tissue damage, risk of infection, etc.

Attempts to mitigate these issues may be categorized in two classes, namely, actively and passively cooled sockets and liners. Actively cooled devices are often highly customized, complex, expensive, bulky, and complication prone, thus limiting their availability and appeal to the majority of amputees. Current passively cooled sockets, such as the Socketless Socket by Martin Bionics, utilize large open areas between radially constrictive solid struts that are lined with pads to achieve volume adjustability, limited fit, and overall cooling. These sockets reduce the area that contact the residual limb, increasing the pressure exerted on small portions of the limb from the downward force of locomotion, frequently causing pain to users.

The contact area between most actively cooled sockets and residual limbs is lower than traditional pin lock or suction sockets, creating pressure points that cause sores and limb damage over time. Sockets also place pressure on the pinnacle of the residual limb, which cannot be subjected to high contact pressure without subjecting the user to significant discomfort.

In consequence of the foregoing considerations, the art continues to seek improved prostheses including transtibial sockets.

SUMMARY

Disclosed herein is a novel transtibial socket for a prosthetic lower limb. A mesh including a plurality of support members and a plurality of tensile members (and further including a plurality of spacer members between different support members in certain embodiments) is arranged between rigid struts, with the mesh allowing for heat dissipation and volume adjustment, while substantially increasing contact area and force distribution around a residual limb. These features enable production of a device with the benefits of a cooled socket, and with the mechanics of a traditional shell suction socket, but with a lower cost.

In one aspect, the disclosure relates to a transtibial socket that comprises a mesh, a plurality of struts, and at least one tensioning member. The mesh is configured to receive a residual limb of an amputee-user, and comprises a plurality of support members and a plurality of tensile members. Each support member of the plurality of support members includes a plurality of passages arranged in different directions. Each tensile member of the plurality of tensile members extends through passages of multiple support members of the plurality of support members. The plurality of struts comprises comprising at least three struts positioned around an interior space configured to receive the mesh, and includes a distal end configured to integrate with a lower leg shaft. The least one tensioning member is coupled with the plurality of tensile members and extends through or past guides defined in the plurality of struts to an adjustable tensioning apparatus. Manipulation of the adjustable tensioning apparatus is configured to selectively tension the at least one tensioning member to allow the mesh to be constricted radially by the amputee-user.

In certain embodiments, the transtibial socket comprises a plurality of spacer members, wherein each spacer member of the plurality of spacer members is arranged between a different pair of the support members of the plurality of support members.

In certain embodiments, each support member of the plurality of support members comprises a hexagonal support member. In certain embodiments, each support member of the plurality of support members comprises a rounded or non-polygonal shape.

In certain embodiments, for each support member, different tensile members of the plurality of tensile members extend through different passages of the plurality of passages. In certain embodiments, for each support member, the plurality of passages includes first, second, and third passages each arranged 120 degrees apart from one another.

In certain embodiments, for each support member, the first, second, and third passages are non-coplanar. In certain embodiments, for each support member, the first second, and third passages each have a substantially rectangular cross-sectional shape.

In certain embodiments, each strut of the plurality of struts comprises an adjustable length.

In certain embodiments, the at least one tensioning member comprises a polymer coated wire. In certain embodiments, the adjustable tensioning apparatus comprises a manually operable rotary tensioning apparatus.

In certain embodiments, the transtibial socket further comprises an adjustable ladder/latch unit enabling a proximal end of the transtibial socket to be radially adjusted around the residual limb of the amputee-user.

In certain embodiments, each support member of the plurality of support members comprises a width or side length, and a width of each spacer member is less than the width or side length of each support member. In certain embodiments, each support member of the plurality of support members comprises a support member thickness, and a thickness of each hollow spacer of the plurality of hollow spacers is less than the support member thickness.

In certain embodiments, each tensile member of the plurality of tensile members comprises a limitedly elastic band.

In certain embodiments, each support member of the plurality of hexagonal members comprises a foam-covered and/or cushioned surface.

In another aspect, a transtibial socket comprises a mesh configured to receive a residual limb of an amputee-user, a plurality of struts, and at least one tensioning member. The mesh comprises a plurality of support members, a plurality of tensile members, and a plurality of spacer members interspersed among the plurality of support members. Each support member of the plurality of support members includes a plurality of passages arranged in different directions. Each tensile member of the plurality of tensile members extends through at least one spacer member of the plurality of spacer members and extends through passages of multiple support members of the plurality of support members. The plurality of struts comprises at least three struts positioned around an interior space configured to receive the mesh, and includes a distal end configured to integrate with a lower leg shaft. The at least one tensioning member is coupled with the plurality of tensile members, and extends through or past guides defined in the plurality of struts to an adjustable tensioning apparatus. Manipulation of the adjustable tensioning apparatus is configured to selectively tension the at least one tensioning member to allow the mesh to be constricted radially by the amputee-user.

In certain embodiments, each support member of the plurality of support members includes a plurality of passages; and for each support member, different tensile members of the plurality of tensile members extend through different passages of the plurality of passages.

In certain embodiments, each strut of the plurality of struts comprises an adjustable length, and the transtibial socket further comprises an adjustable ladder/latch unit enabling a proximal end of the transtibial socket to be radially adjusted around the residual limb of the amputee-user.

In certain embodiments, for each support member of the plurality of support members, the plurality of passages includes first, second, and third passages each arranged 120 degrees apart from one another, and the first, second, and third passages are non-coplanar.

Additional aspects of the present disclosure relate to a method for fabricating transtibial sockets, and to prostheses including transtibial sockets disclosed herein.

In another aspect, any one or more aspects or features described herein may be combined with any one or more other aspects or features for additional advantage.

BRIEF DESCRIPTION OF DRAWINGS

The accompanying drawings incorporated in and forming a part of this specification illustrate several aspects of the disclosure, and together with the description serve to explain the principles of the disclosure.

FIG. 21A is a perspective view of a transtibial socket including variable length strut sections according to one embodiment of the present disclosure.

FIG. 21B is a side elevational view of one strut of the transtibial socket of FIG. 21A.

DETAILED DESCRIPTION

Figure 1:
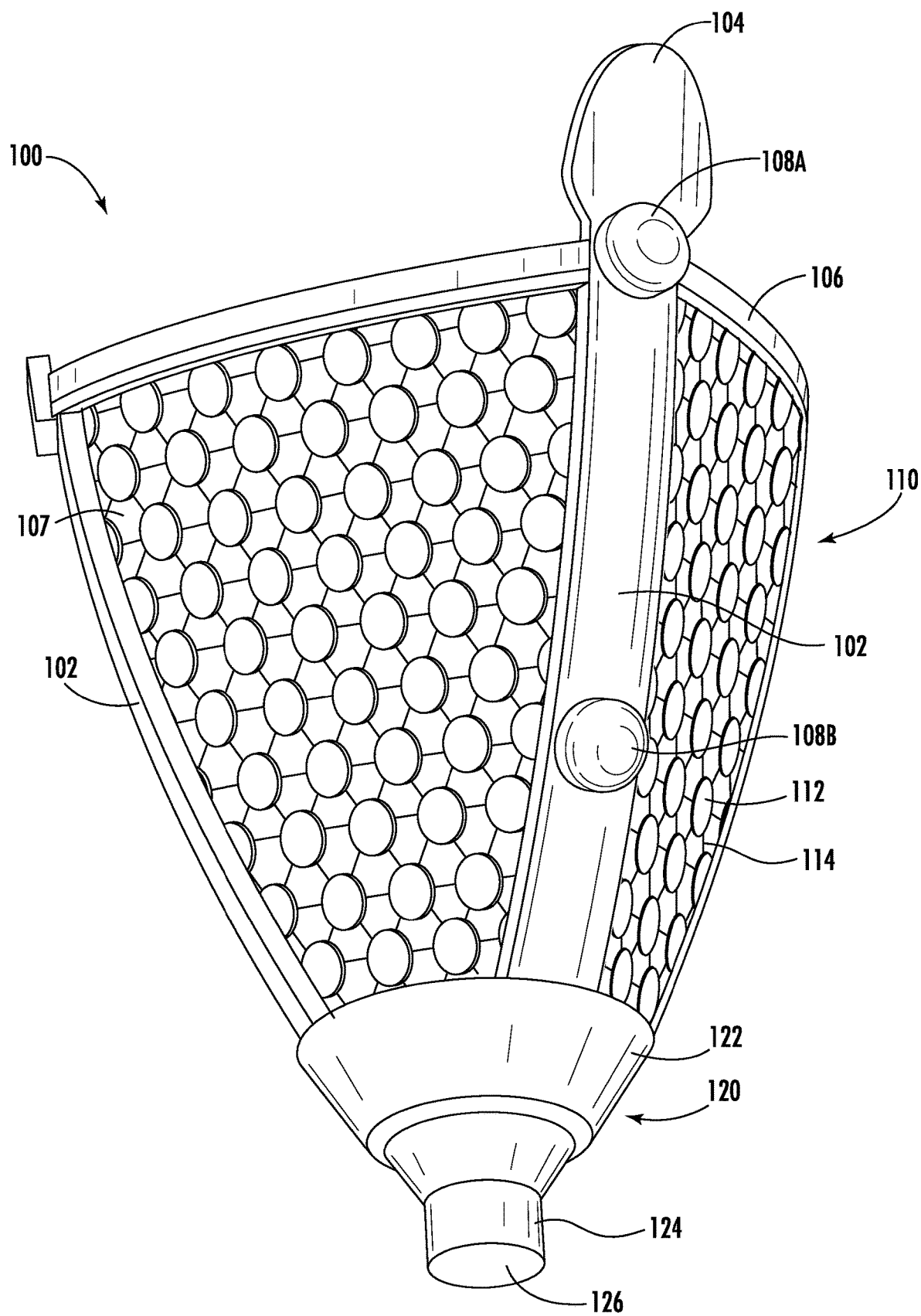
FIG. 1 is a perspective view illustration of a first transtibial socket including a mesh of a plurality of generally round support members and a plurality of tensile members supported by multiple (e.g., three) rigid struts, according to one embodiment of the present disclosure.

Disclosed herein are novel prosthetic devices as well as methods for their manufacture and use. In certain embodiments, a transtibial socket utilizes a mesh that includes support members, spacers, and tensile bands arranged between rigid struts, with the mesh being arranged between a plurality of rigid struts. Air gaps are provided between different support members. The mesh allows for heat dissipation and volume adjustment, while substantially increasing contact area and force distribution around a residual limb relative to actively cooled sockets, but without the cost and complexity of actively cooled sockets. The mesh may be radially flexible to allow for a full range of motion, while having sufficient vertical rigidity to ensure comfortable weight support. Restated, the mesh permits constriction without loss of rigidity, while still providing numerous pathways for air circulation. By creating a transtibial socket structure that produces distributed air gaps across the surface it covers, air can pass through the socket structure and passively cool the residual limb of a user by circulation and sweat evaporation. Such passive cooling is intended to provide sufficient airflow and heat dissipation to mimic the conditions of a healthy limb environment, in a structure that provides the mechanics of a traditional shell suction socket.

Benefits of transtibial sockets according to embodiments disclosed herein is that they: are breathable; exhibit minimal energy loss in translation; contour to a variety of residual limb shapes and size; provide passive cooling of a residual limb; are adjustable by a patient to accommodate limb swelling or contraction throughout the day; are as simple to use as, or simpler to use than, currents; durable for many on/off cycles over time; minimize tissue damage; distribute forces radially around a residual limb thereby prevent impingement of pressure points on the pinnacle of a residual limb; and are comfortable to wear and use.

Before going into detail regarding particular embodiments, various desirable characteristics of transtibial sockets according to various embodiments will be identified, to enable appreciation of the multitude of factors that may be considered. Desirable characteristics may include some or all of the following: enablement of moisture wicking; easy application and removal; enhancement of ventilation (e.g., to address smell, enable heat release, and inhibit bacterial growth); durability; shock absorptiveness; ability to be sized and scaled for a wide range of patients; ability to comfortably support patients of differing weights; promotion of even force distribution; inhibition of abnormal loading; avoidance of pain (e.g., due to abrasion, pinching, weight distribution, chemical irritation, etc.); adjustability by patient (including intra-day adjustment to accommodate residual limb swelling or dimensional variation); customizability for patients; enhanced user comfort; stays on user during activity; easy integration with lower leg portion; and reparability with replacement parts. Various embodiments herein address some or all of the foregoing desirable characteristics.

In certain embodiments, a transtibial socket includes three or more struts that extend upward (e.g., and outward) relative to a strut/shaft interface. In certain embodiments, intermediate and/or upper portions of the struts may be joined by one or more transverse members, optionally arranged in a partial or complete ring. Examples of suitable materials for fabricating struts and/or transverse members include carbon fiber, metal, composites (including fiber-reinforced composites), laminates, the like, and combinations of the foregoing. Multiple struts in combination with a strut/shaft interface (optionally including one or more transverse members), may be referred to herein as a strut body. In various embodiments, a strut body defines a substantially cup-like shape with generally open sides to accommodate presence of a mesh within the strut body without inhibiting airflow to the mesh body. In certain embodiments, a strut body may be fabricated by one or more of molding, thermoforming, machining, three-dimensional printing, sintering, welding, or the like. In certain embodiments, struts of a strut body may comprise an adjustable height, in order accommodate residual limb portions of different lengths.

In certain embodiments, one or more portions of a strut body may define guides or openings to permit passage of one or more tensioning members that are coupled within tensile members of a mesh. For example, one or more tensioning members may extending through or past guides defined in struts and/or transverse members of a strut body. In certain embodiments, one or more tensioning members may comprise wires. In certain embodiments, one or more tensioning apparatuses (e.g., suitable for permitting a user to adjust tension applied to tensile members of a mesh) may be supported by various portions of a strut body. Such application of tension may permit a mesh to be constricted (e.g., radially constricted) by a user. In certain embodiments, a first tensioning apparatus may be arranged proximate to an upper portion of a strut body, and a second tensioning apparatus may be arranged between an upper portion of the strut body and a strut/shaft interface arranged at a lower portion of the strut body.

In certain embodiments, a mesh may comprise a plurality of support members and a plurality of tensile members that extending through passages defined in the support members. For example, each support member may define multiple passages arranged in different directions. In certain embodiments, each passage within a support member is arranged about 90 to 120 degrees apart from at least one other passage of the support member. In certain embodiments, various passages defined within a support member may be coplanar or non-coplanar in character. Use of non-coplanar passages may be beneficial to prevent interference or frictional binding between adjacent tensile members.

In certain embodiments, tensile members of a mesh may comprise wires, bands, strings, composites, or the like. In certain embodiments, tensile members of a mesh may comprise limitedly elastic materials, thereby providing a small but limited degree of stretch (as may be desirable for shock absorption). In certain embodiments, tensile members of a mesh may include low-friction surface coatings or layers to inhibit frictional binding between adjacent tensile members within a support member and/or frictional binding between tensile members and a support member.

In certain embodiments, passages defined in support members may comprise generally rectangular cross-sectional shapes (e.g., having a greater width than height) to accommodate generally flat tensile members of similar cross-sectional shapes. In certain embodiments, passages defined in support members may comprise round, oval, or other cross-sectional shapes.

Support members may comprise any suitable shape or shapes to provide a mesh configured to receive a residual limb of a user. In certain embodiments, support members may comprise generally hexagonal, octagonal, or other polygonal shapes, optionally with rounded vertices. In certain embodiments, support members may comprise round, oval, elliptical, other rounded shapes, or other non-polygonal shapes. In certain embodiments, support members may comprise a cushioned (e.g., foam covered) surface configured to contact skin of a residual limb. In certain embodiments, support members may comprise polymeric, elastomeric, composite, or other materials, and may be fabricated by molding, stamping, die cutting, waterjet cutting, laser cutting, three-dimensional printing, or similar methods.

In certain embodiments, spacer members may be provided between support members, in order to maintain a desired spacing between support members (e.g., to facilitate airflow, prevent pinching of a user's skin between support members, etc.). For example, spacer members may be interspersed among support members In certain embodiments, each spacer member may comprise a width that is less than a width or side length of at least one adjacent support member. In certain embodiments, each spacer member defines an aperture through which one or more tensile members may extend. Such an aperture may have any suitable cross-sectional shape, such as rectangular, round, oval, or the like. In certain embodiments, an aperture defined through a spacer member may comprise a width that is at least three times, at least five times, or at least ten times greater than a height thereof. In certain embodiments, a portion of a spacer member may abut a surface of an adjacent support member or protrude into a passage defined in an adjacent support member.

FIG. 1 is a perspective view illustration of a first transtibial socket 100 including a mesh 110 formed of a plurality of support members 112 and a plurality of tensile members 114, with the mesh 110 being supported by multiple (e.g., three) struts 102 of rigid material according to one embodiment of the present disclosure. As shown, the support members 112 are generally round in shape, and the tensile members 114 extend in multiple directions to interconnect the support members 112 to form the mesh 110. A ring-shaped transverse member 106 interconnects the struts 102 proximate to upper ends 104 thereof, and a base 120 is connected to bottom ends of the struts 102. In certain embodiments, the ring-shaped transverse member 106 may be embodied in an adjustable ladder/latch assembly that enables an upper or proximal end of the transtibial socket 100 to be radially adjusted around a residual limb of the amputee-user. The base 120 includes a tapered outer surface 122 and strut/shaft interface portion 124 defining a receptacle 126 configured for permitting attachment of a prosthetic limb portion (not shown). Gaps or windows 107 are provided between the struts 102, wherein the mesh 110 extending across the gaps or windows 107 between the struts 102. The mesh 110 may be attached to the transverse member 106 as well as the struts 102. Tensioning members 108A, 108B associated with the struts may be provided to enable a user to adjust a tension applied to the tensile members 114, thereby adjusting tightness of the mesh 102 around a user's residual limb received within the transtibial socket 100. The mesh 110 has a generally frustoconical shape that is wider at the top and narrower at the bottom.

Figure 2:
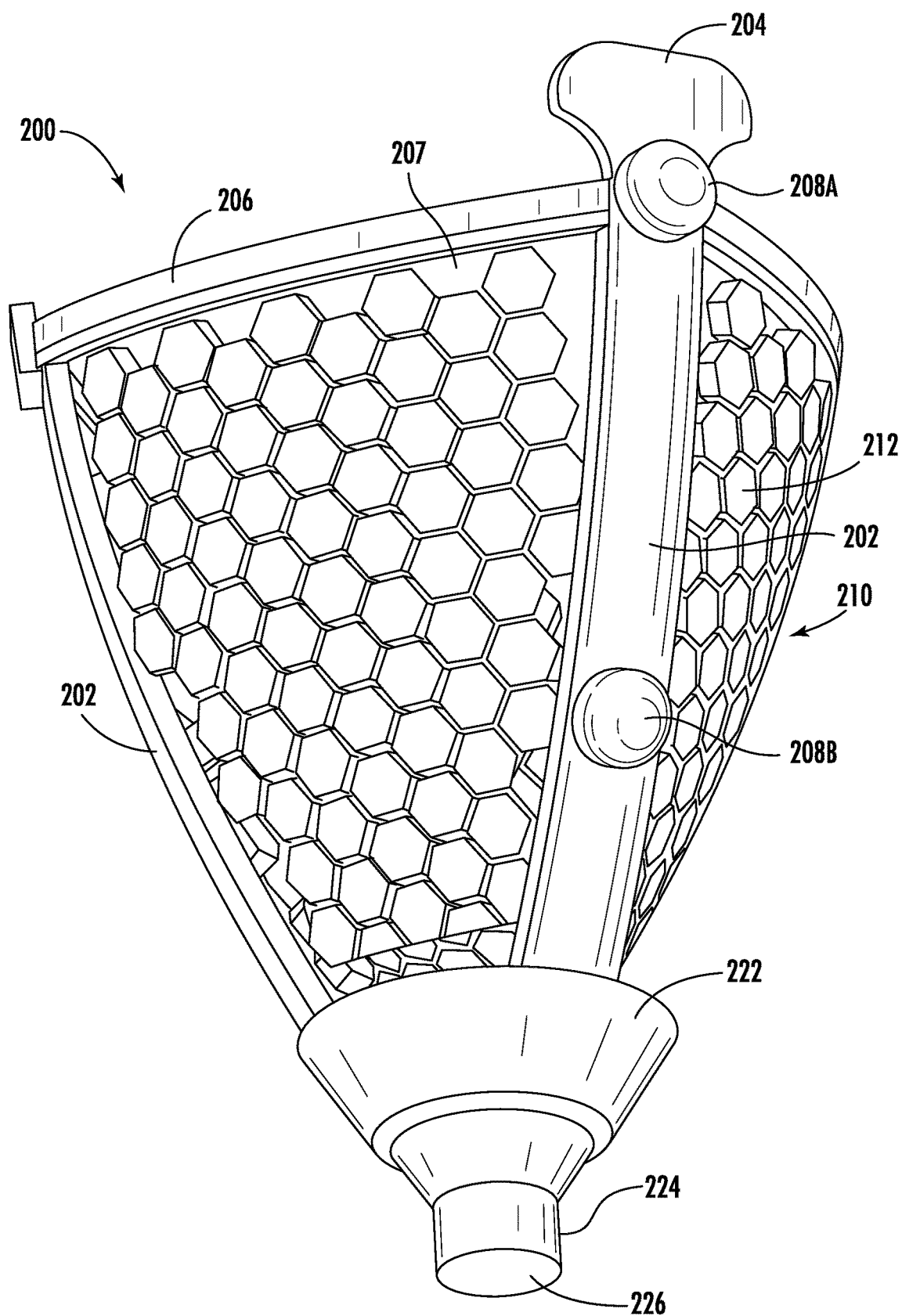
FIG. 2 is a perspective view illustration of a first transtibial socket including a mesh of a plurality of generally hexagonal support members and a plurality of tensile members supported by a three rigid struts, according to one embodiment of the present disclosure.

FIG. 2 is a perspective view illustration of another transtibial socket 200 including a mesh 210 formed of a plurality of support members 212 and a plurality of tensile members (not shown) supported by multiple (e.g., three) struts 202 of rigid material according to one embodiment of the present disclosure. Each support member 112 is generally rectangular in shape and defines passages extending in different directions through which tensile members extend. A ring-shaped transverse member 206 interconnects the struts 202 proximate to upper ends 204 thereof, and a base 220 is connected to bottom ends of the struts 202. In certain embodiments, the ring-shaped transverse member 206 may be embodied in an adjustable ladder/latch assembly (e.g., including a ladder-type strap and a releasable latch) that enables an upper or proximal end of the transtibial socket 200 to be radially adjusted around a residual limb of the amputee-user. The base 220 includes a tapered outer surface 222 and a strut/shaft interface portion 224 defining a receptacle 226 configured for permitting attachment of a prosthetic limb portion (not shown). Gaps or windows 207 are provided between the struts 202, wherein the mesh 210 extending across the gaps or windows 207 between the struts 202. The mesh 210 may be attached to the transverse member 206 as well as the struts 202. Tensioning members 208A, 208B associated with the struts may be provided to enable a user to adjust a tension applied to the tensile members 214, thereby adjusting tightness of the mesh 202 around a user's residual limb received within the transtibial socket 200.

Figure 3:
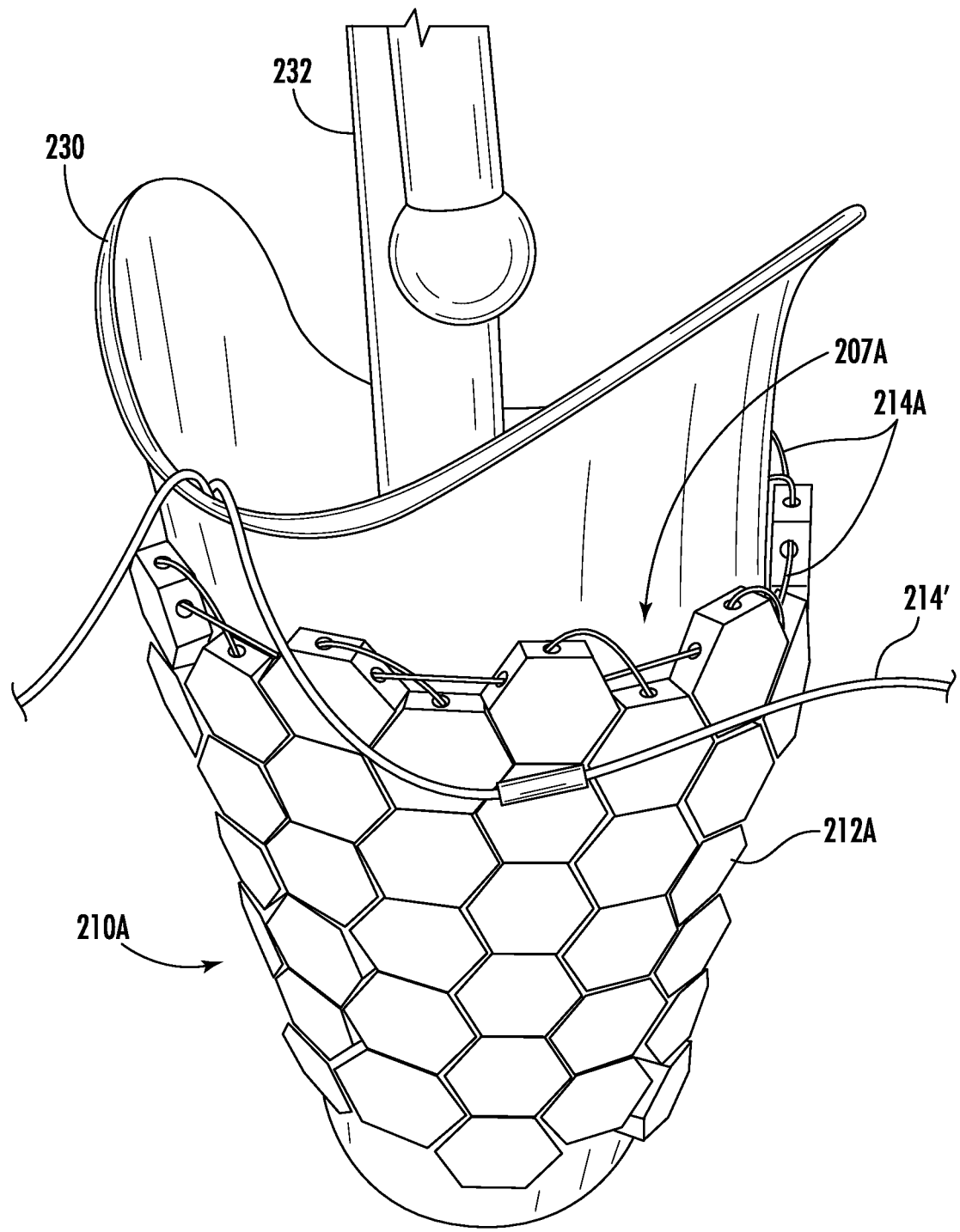
FIG. 3 is a perspective view illustration of a mesh of hexagonal support members and tensile members arranged in a generally frustoconical shape in preparation for force distribution testing.

FIG. 3 is a perspective view illustration of a mesh 210A of support members 212A (each having a hexagonal shape) and tensile members 214A arranged in a generally frustoconical shape within a tapered form 230 having an associated piston 232 in preparation for force distribution testing of the mesh 210A. As shown, the tensile members 214A extend through round passages defined in multiple directions through the support members 212A. Tensioning members 214 (which may embody extensions of selected tensile members 214A) are show as extending through the tapered form 230 and may be retained in a taut state to cause the mesh 210A to conform around an exterior surface of the tapered form 230. During force distribution testing, the piston 232 may be pushed downward into a rigid fill material within the tapered form 230 to expand the tapered form 230 and thereby pressure exerted against the support members 212. Pressure sensors (not shown) may be provided between the support members 212 and the tapered form 230 to measure pressure exerted against the support members 212.

Figure 4A:
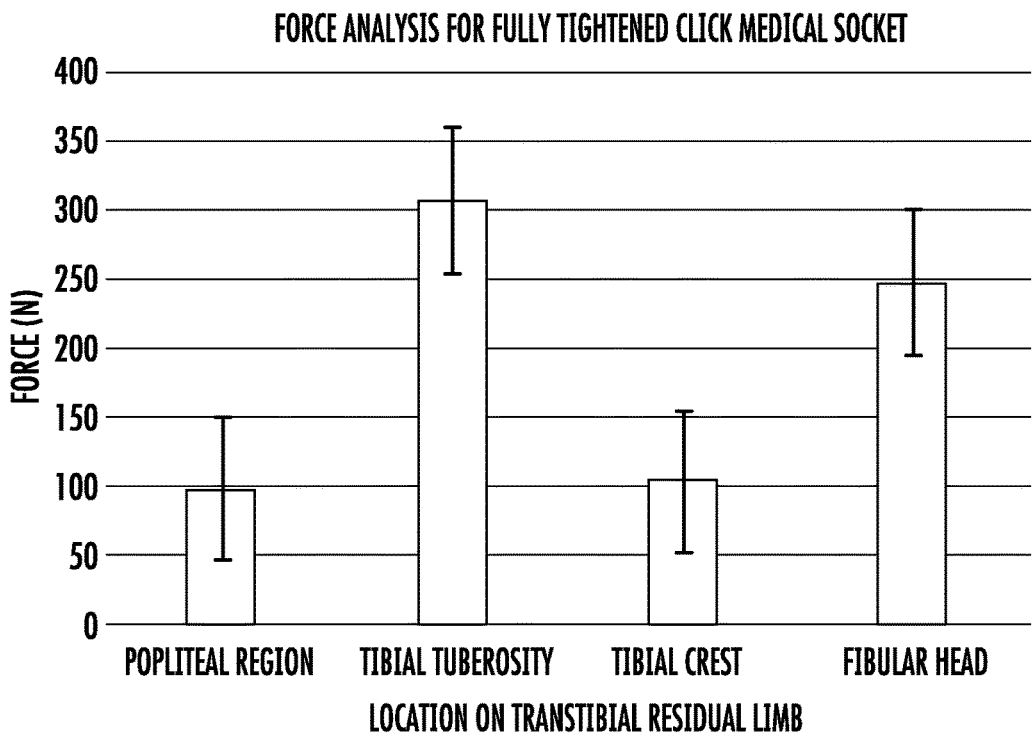
FIG. 4A is a bar chart providing maximum force readings on different regions (popliteal region, tibial tuberosity, tibial crest, and fibular head) of a residual limb using a conventional Click Medical RevoFit transtibial socket in a fully tightened state.
Figure 4B:
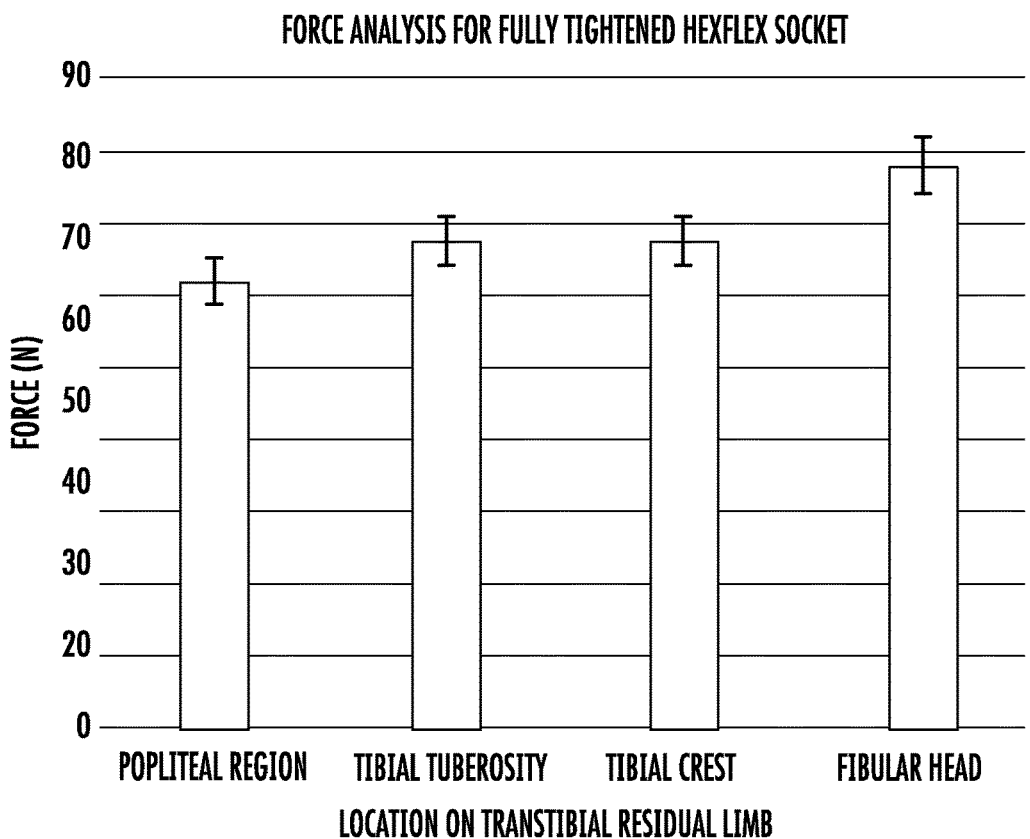
FIG. 4B is a bar chart providing maximum force readings on different regions (popliteal region, tibial tuberosity, tibial crest, and fibular head) of a residual limb using a transtibial socket according to one embodiment of the present disclosure.

FIG. 4A is a bar chart providing maximum force readings on different regions (popliteal region, tibial tuberosity, tibial crest, and fibular head) of a residual limb using a conventional Click Medical RevoFit transtibial socket in a fully tightened state, showing forces ranging from about 100 N to about 300 N. Maximum force was experienced at the tibial tuberosity region. FIG. 4B is a bar chart providing maximum force readings on different regions (popliteal region, tibial tuberosity, tibial crest, and fibular head) of a residual limb using a transtibial socket according to one embodiment of the present disclosure, showing forces in a range of between 60 N and 80 N. A comparison of FIGS. 4A and 4B shows that average and maximum forces imposed on the residual limb are much lower for the transtibial socket according the present disclosure, and that variation in applied force among the different regions is substantially smaller. This shows that the transtibial socket according the present disclosure distributed pressure more evenly around the residual limb than the Click Medical RevoFit socket.

Figure 5:
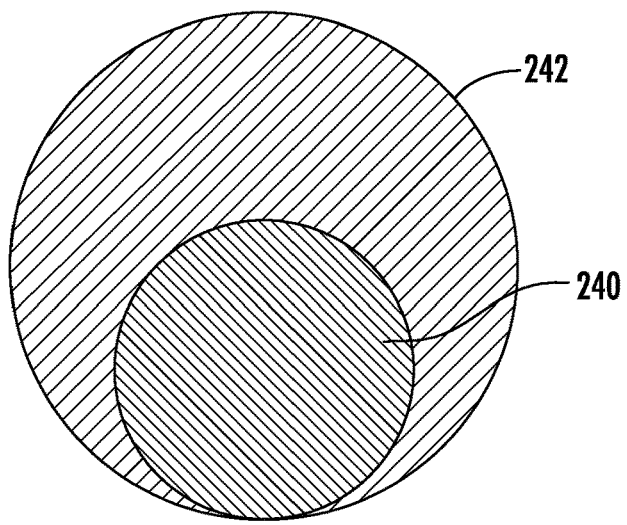
FIG. 5 is a graphic providing a scale comparison of compressive areas provided by a transtibial socket according to one embodiment of the present disclosure, and by a Click Medical RevoFit socket.

FIG. 5 is a graphic providing a scale comparison of a compressive area 242 provided by a transtibial socket according to one embodiment of the present disclosure, and a compressive area 240 provided by a Click Medical RevoFit socket. The transtibial socket embodiment according to the present disclosure (including support members each having a hexagonal shape connected by tensile members into a mesh) exhibited a surface area of force distribution of 422.45 cm$^2$ and a tightening force of 66.723 N was applied. In comparison, the Click Medical RevoFit socket exhibited a surface area of force distribution of 149.09 cm$^2$ and a tightening force of 355.858 N was applied. A scaling factor of 5.33 was taken into account when converting base force scaling resistor (FSR) readings into Newtons.

Figure 6:
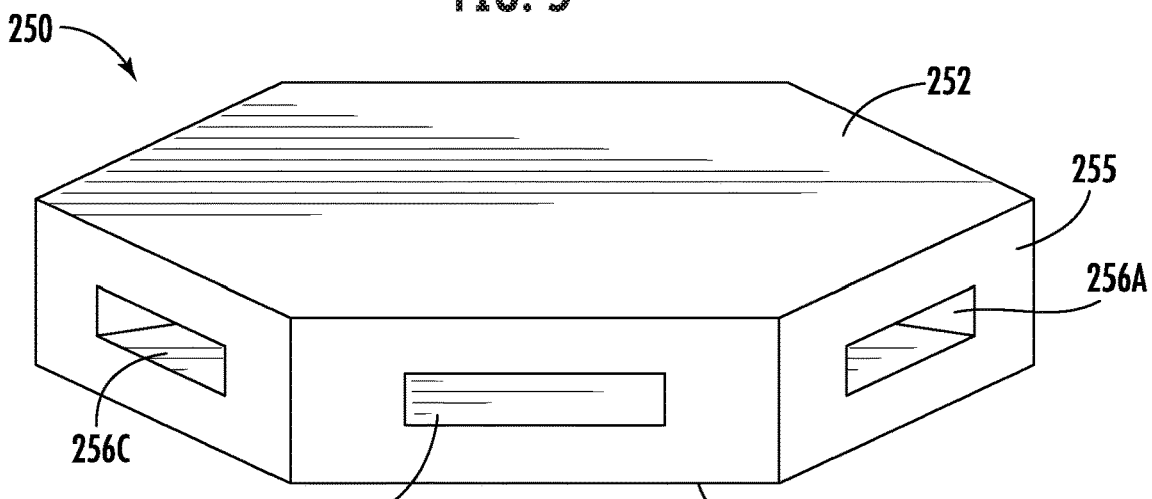
FIG. 6 is perspective view illustration of a support member according to one embodiment, with the support member being hexagonal in shape and defining substantially coplanar first, second, and third passages each having a rectangular cross-sectional shape and being arranged 120 degrees apart from one another.

FIG. 6 is a perspective view illustration of a support member 250 according to one embodiment. The support member 250 is hexagonal in shape with six sidewalls 255 extending between first and second faces 251, 252 thereof. Substantially coplanar first, second, and third passages 256A-256C extending through the sidewalls 255 each have a rectangular cross-sectional shape and are arranged 120 degrees apart from one another. One concern with the coplanar character of the passages 256A-256C is that tensile members (not shown, but optionally provided as wide, thin bands) threaded through the passages 256A-256C may bind and/or interfere with one another, depending on relative thicknesses of the tensile members and the passages 256A-256C. To address this concern, support members may be provided with non-coplanar passages, as described in the next figure.

Figure 7:
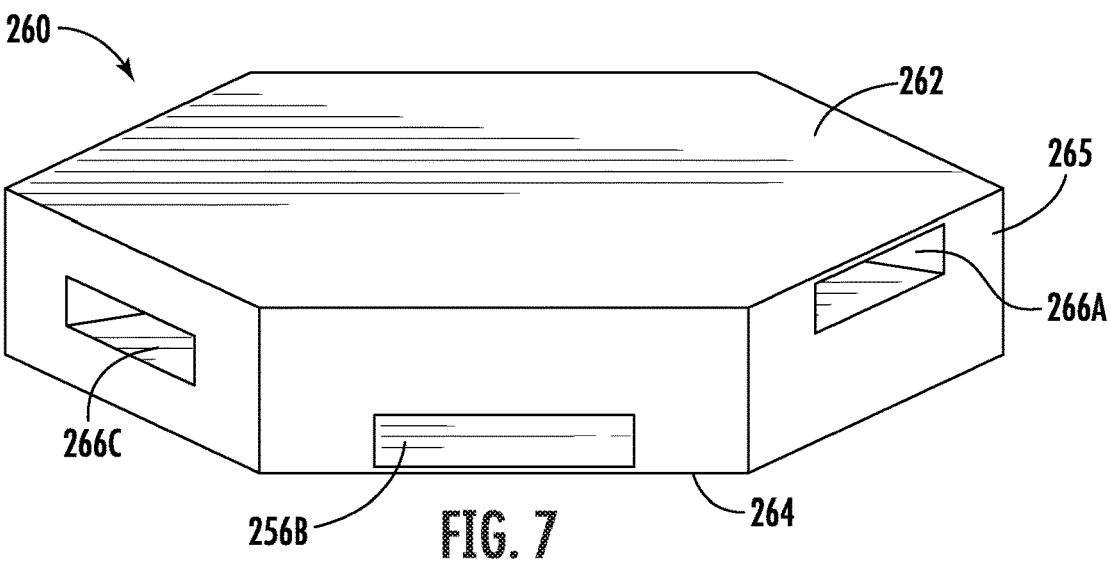
FIG. 7 is a perspective view illustration of a support member according to one embodiment, with the support member being hexagonal in shape and defining non-coplanar first, second, and third passages each having a rectangular cross-sectional shape and being arranged 120 degrees apart from one another.

FIG. 7 is a perspective view illustration of support member 260 according to one embodiment. The support member 260 is hexagonal in shape with six sidewalls 255 extending between first and second faces 261, 262 thereof. Non-coplanar first, second, and third passages 266A-266C extending through the sidewalls 265 each have a rectangular cross-sectional shape and are arranged 120 degrees apart from one another. The first passage 266A arranged in a first plane closer to the first face 261, the second passage 266B is arranged in a second plane closer to the second face 262, and the third passage 266C is arranged in a third plane equidistantly positioned between the first and second faces 261, 262. Each passage 266A-266C has a height that is substantially thinner than a height of the support member 260, has a width that is narrower than a side length of the support member 260, and has a generally rectangular cross-sectional shape. Such dimensions permit airflow between support members connected by bands and spacers within a mesh, as will be illustrated hereinafter. Passages 266A-266C as permit the use of tensile members (not shown) in the form of relatively thin, wide bands to construct a mesh, thereby lessening the thickness of such tensile members relative to the use of tensile members of round or square cross-sectional shapes of comparable cross-sectional area.

Figure 8:
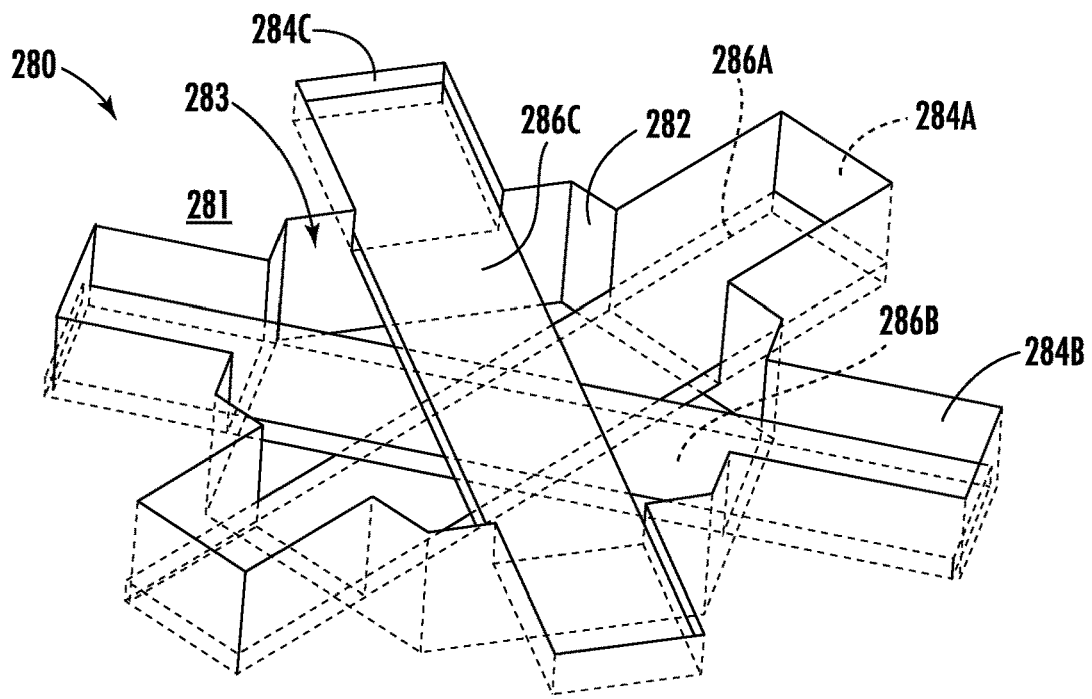
FIG. 8 is a perspective view of a cavity portion of a mold including three non-coplanar or "lofted" cross-beams that may be used during a molding fabrication process to form passages in a support member of a hexagonal shape for fabricating a mesh of a transtibial socket according to one embodiment, including hidden features represented in dashed line format.
Figure 9:
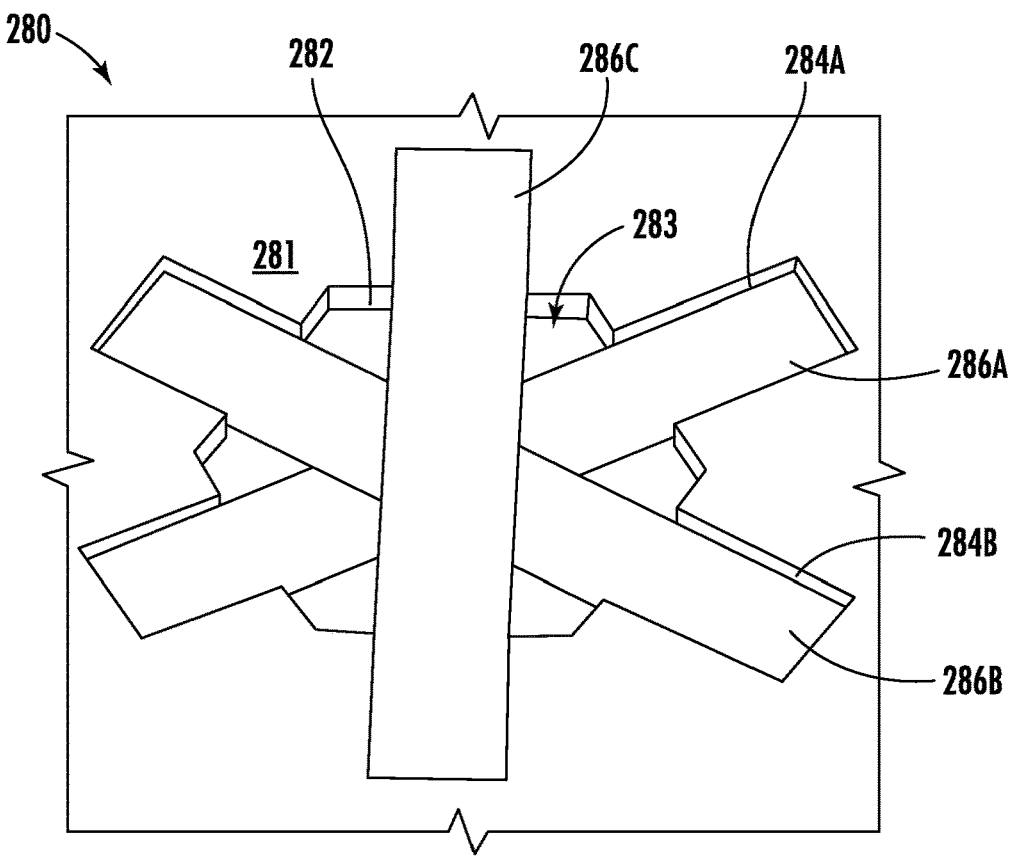
FIG. 9 is a perspective view of the mold cavity portion of FIG. 8 containing three non-coplanar cross-beams, omitting hidden features.

FIGS. 8 and 9 illustrate a mold 280 including a body 281 defining a central cavity 283 bounded by cavity walls 282 and including three cavity extensions 284A-284C of different depths, with the cavity extensions 284A-284C containing non-coplanar or "lofted" cross-beams 286A-286C that may be used during a molding fabrication process to form passages within a hexagonal member. In FIG. 8, hidden features are shown in dashed line format, whereas FIG. 9 is devoid of hidden features. The cross-beams 286A-286C may be placed in the mold 280. Thereafter, molding material may be supplied to the central cavity 282 and cavity extensions 284A-284C and solidified. After solidification, the cross-beams 286A-286C may be removed. In certain embodiments, the cross-beams 296A-286C may be fabricated of fiberboard, metal, polymeric, or composite materials.

Figure 10:
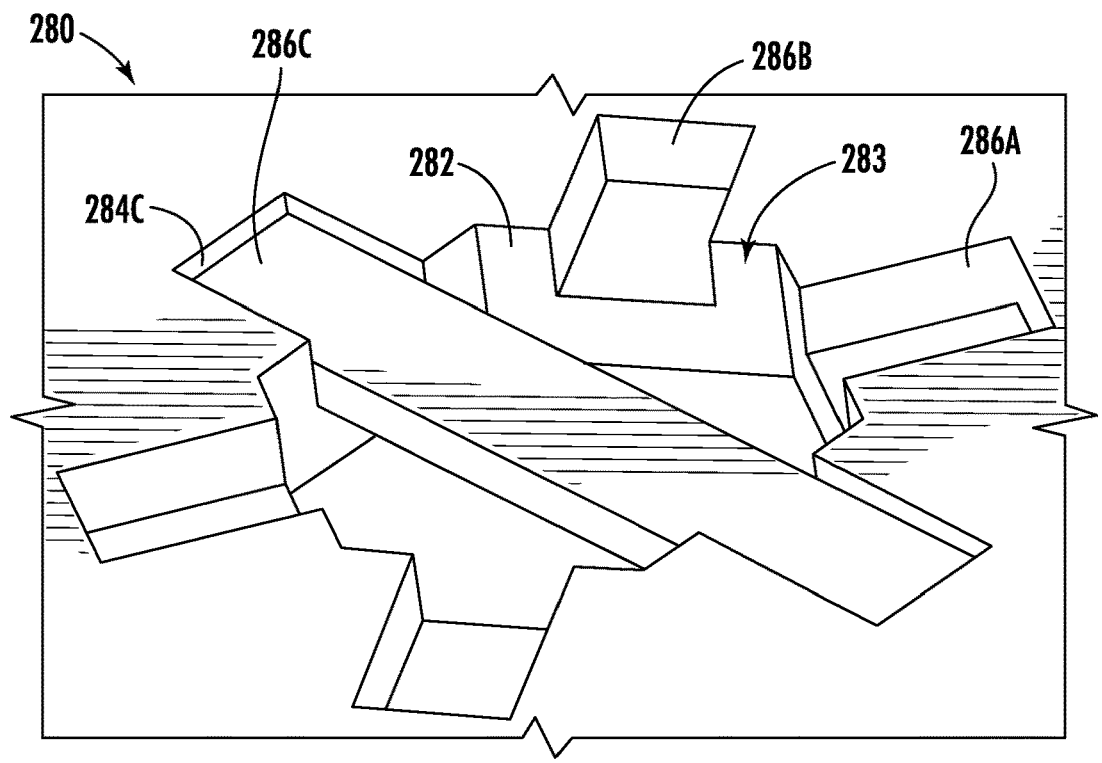
FIG. 10 is a perspective view of at least a portion of a mold according to the design of FIGS. 8 and 9, containing a single cross-beam.

FIG. 10 is a perspective view of at least a portion of a mold 280 according to the design of FIGS. 8 and 9, including a central cavity 283 bounded by cavity walls 282 and including three cavity extensions 284A-284C of different depths, with a single cross-beam 286C extending across the central cavity 283 in one cavity extension 284C.

Figure 11:
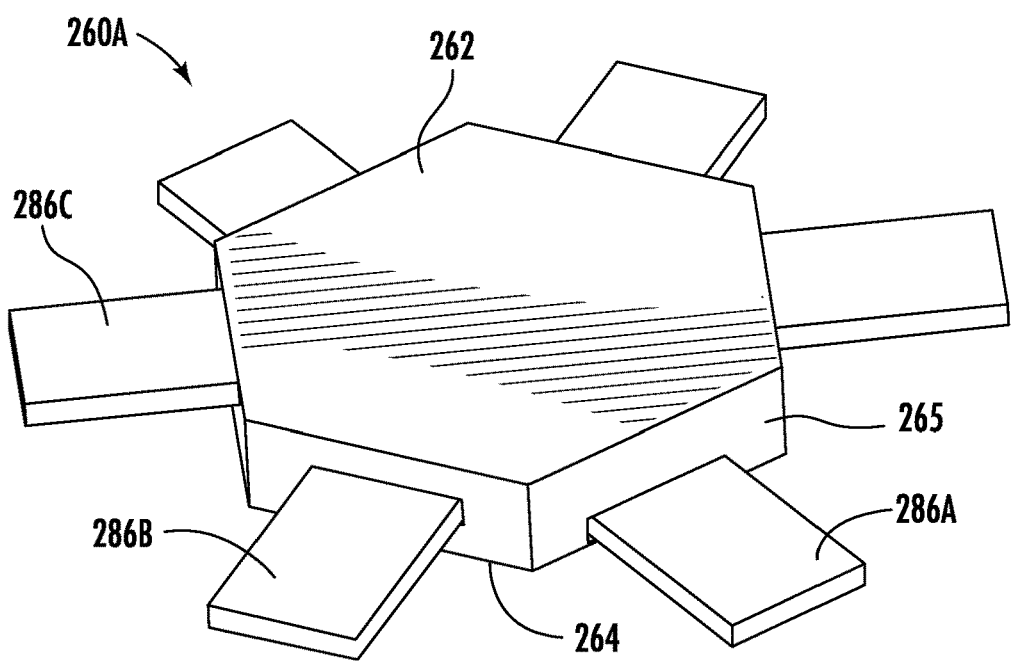
FIG. 11 is a perspective view of a single support member having a hexagonal shape with three non-coplanar cross-beams contained therein for producing passages and produced by a mold according to FIGS. 8-10.

FIG. 11 is a perspective view of a single support member 260A having a hexagonal shape with six sidewalls 265 extending between upper and lower surfaces 262, 264 thereof, with three non-coplanar cross-beams 286A-286C for producing passages retained within the support member 260A. The support member 260A may be produced by a mold 280 as illustrated in FIGS. 8-10.

Figure 12:
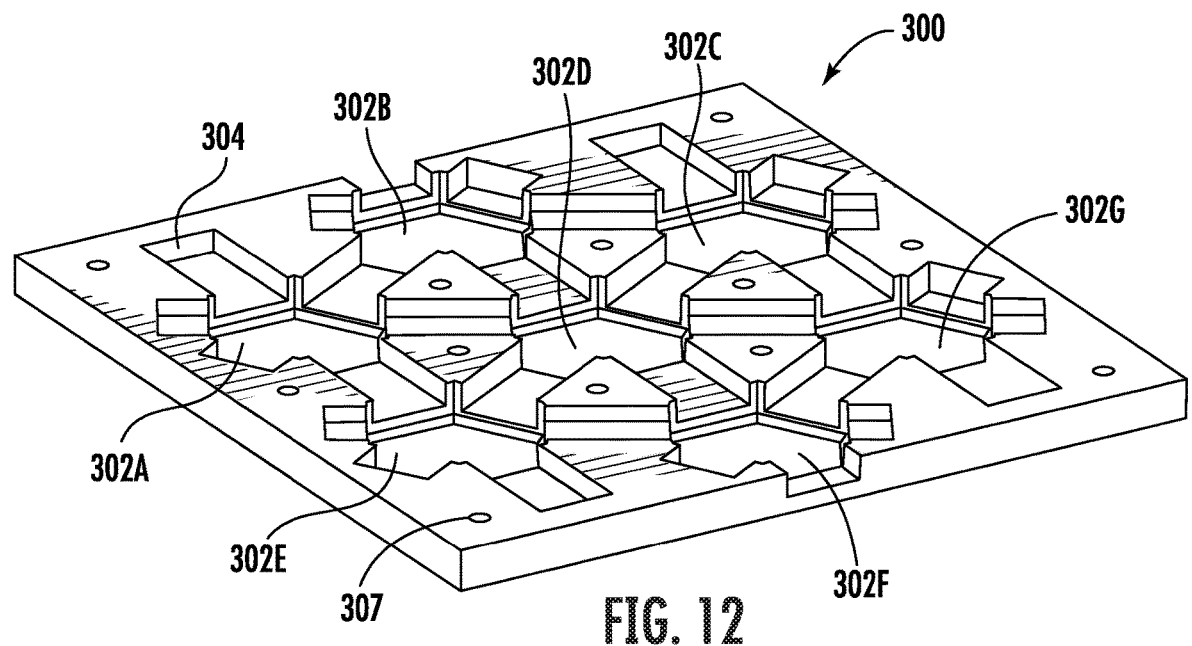
FIG. 12 is a perspective view illustration of a mold for receiving multiple intersecting cross-members and suitable for producing seven (7) hexagonal support members each being hexagonal in shape and defining non-coplanar first, second, and third passages therein.
Figure 13:
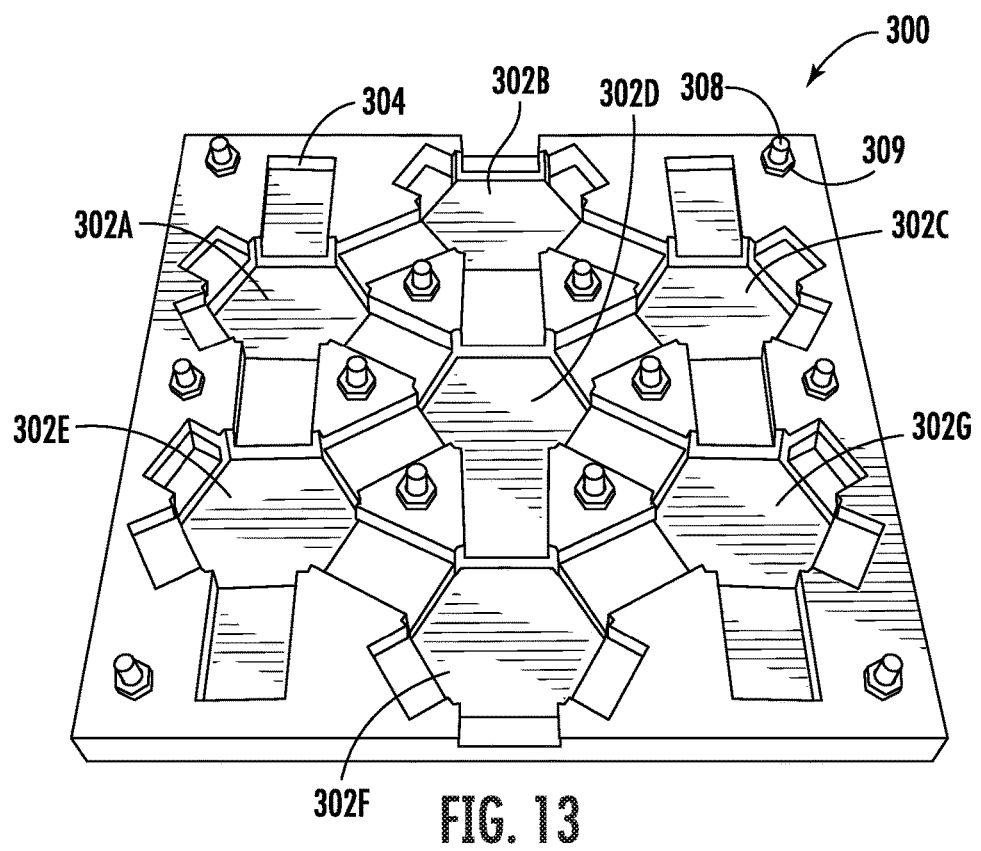
FIG. 13 is a perspective view illustration of the mold of FIG. 12 with addition of threaded studs and nuts suitable for securing a flat cover (not shown) over an upper surface of the mold.

FIG. 12 is a perspective view illustration of a mold 300 (e.g., a gang-style mold) including cavity extensions 304 for receiving multiple intersecting cross-members and including central cavities 302A-302G suitable for producing seven (7) support members each being hexagonal in shape and defining non-coplanar first, second, and third passages therein. The mold 300 further includes holes 307 for receiving fasteners (not shown) for affixing a cover to the mold 300. FIG. 13 is a perspective view illustration of the mold 300 of FIG. 12 with the addition of threaded studs 308 and nuts 309 suitable for securing a cover (not shown) over an upper boundary of the mold 300 (e.g., after cross-members and flowable material have been received by the mold 300). Any suitable material may be used for fabricating hexagonal members using molds, such as molten polymers, curable resins, epoxies, and the like. In certain embodiments, air cured resin may be used.

In certain embodiments, support members of a transtibial socket may be fabricated from multiple discrete layers of material to permit formation of non-coplanar passages. One such example is shown in FIG. 14.

Figure 14:
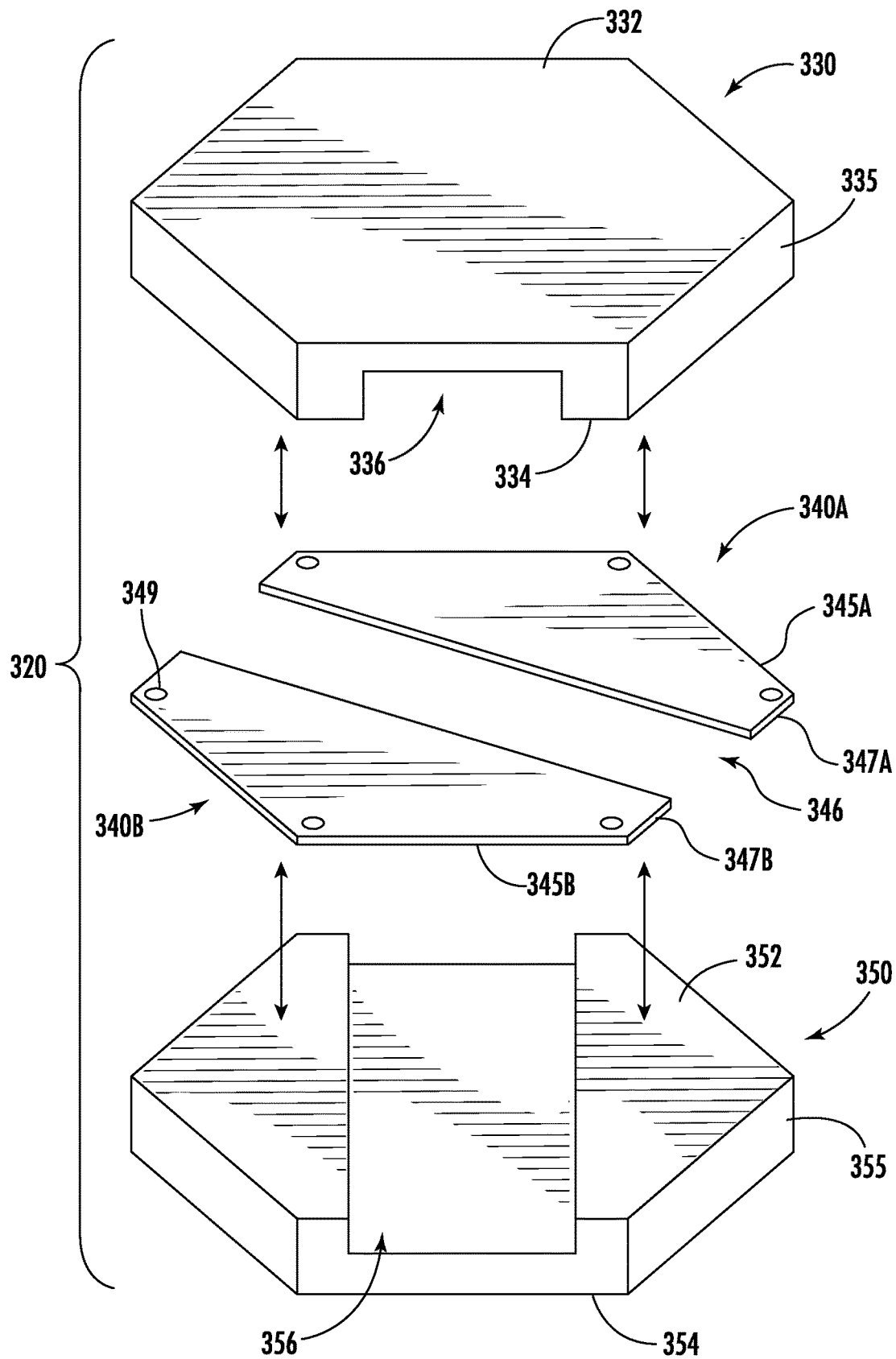
FIG. 14 is an exploded perspective view illustration of components of a multi-layer support member having a hexagonal shape and defining three non-coplanar passages therein, including upper and lower layers with an intermediate layer arranged therebetween.

FIG. 14 is an exploded perspective view of a support member 320 having a hexagonal shape and being fabricated from multiple layers of material. A topmost layer 330 includes six sidewalls 335 extending between an upper surface 332 and a lower surface 334, with a first recess 336 suitable for forming a first passage being defined in the lower surface 334. A middle layer may be formed of two middle layer portions 340A, 340B that are spaced apart from one another by a gap 346 suitable for forming a second passage. Each middle layer portion 340A, 340B includes two full width sidewall portions 345A, 345B and two reduced width sidewall portions 347A, 347B. Holes 349 defined in the middle layer portions 340A, 340B may receive fasteners (not shown) for coupling the middle layer portions 340A, 340B between the topmost layer 330 and a bottom layer 350. The bottom layer 350 includes six sidewalls 355 extending between an upper surface 352 and a lower surface 354, with a third recess 356 suitable for forming a third passage being defined in the upper surface 352. When the middle layer portions 340A, 340B are coupled between the topmost layer 330 and the bottom layer 350 (e.g., with pins, screws, adhesives, or any other suitable joining methods), the first recess 336, the gap 346, and the third recess 356 are non-coplanar and are each oriented 120 degrees apart from one another.

Figure 15:
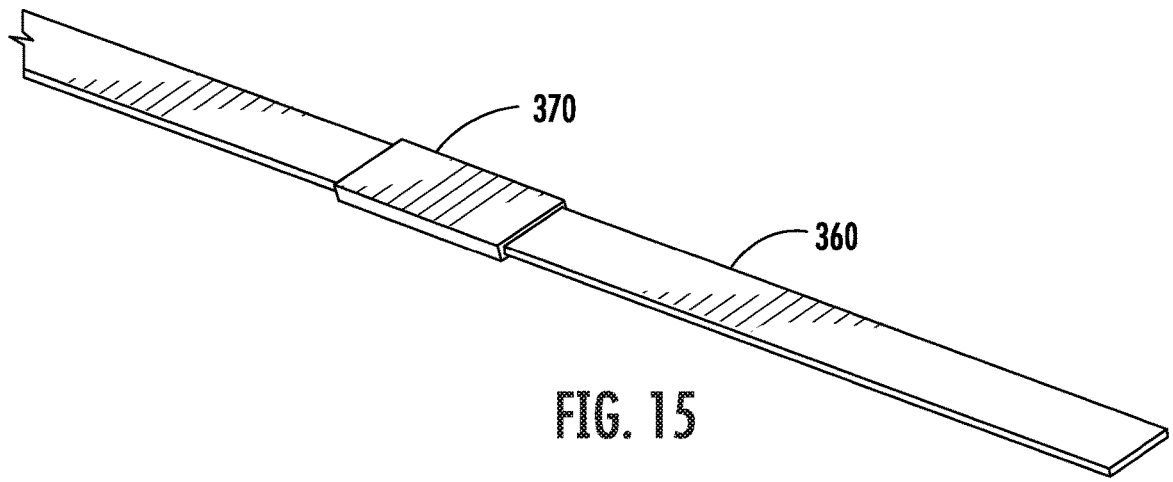
FIG. 15 is a perspective view illustration of a tensile member in the form of a flat, limitedly flexible band (or strap), following insertion through an aperture defined by hollow spacer member having a generally rectangular shape.
Figure 16:
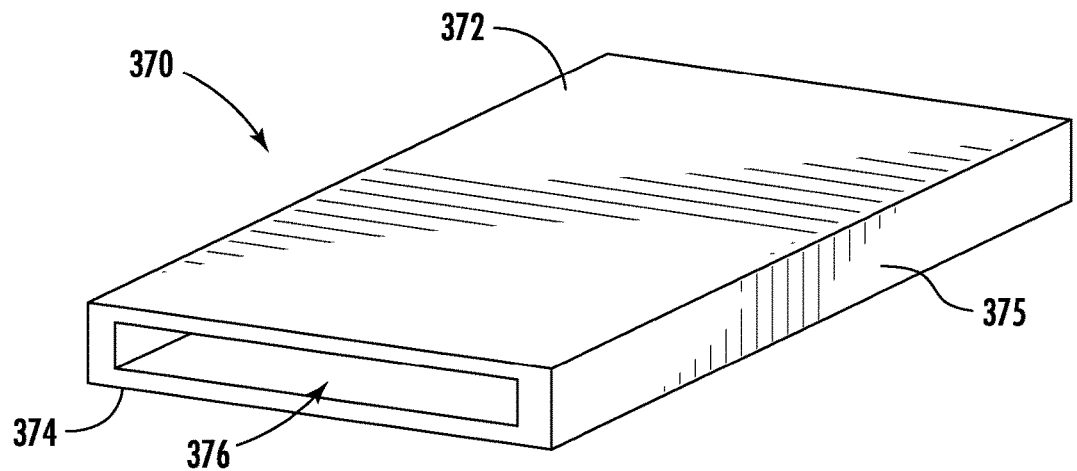
FIG. 16 is a magnified, perspective view illustration of the hollow spacer member of FIG. 15.

FIG. 15 is a perspective view illustration of a tensile member 360 in the form of a flat, limitedly flexible band (or strap), following insertion of the tensile member 360 through an aperture (e.g., having a generally rectangular cross-sectional shape) defined by a spacer member 370. FIG. 16 is a perspective view of the spacer member 370, showing sidewalls 375 extending between top and bottom walls 372, 372, with an aperture 376 (having a rectangular cross-sectional shape including a width that is more than five times greater than its height) defined between two ends thereof. In certain embodiments, multiple spacer members 370 according to the design of FIG. 16 may be interspersed among multiple support members (not shown), with tensile members extending through respective tensile members and support members to form a mesh of a transtibial socket. In such an instance, spacer members 370 may be used to induce localized rigidity when a mesh is constricted around a residual limb. In certain embodiments, spacer members 370 may comprise a polymeric material such as HDPE. In certain embodiments, tensile members configured to cooperate with spacer members and support members may comprise synthetic or natural rubber, optionally reinforced with fibers, wires, threads, or the like.

Figure 17:
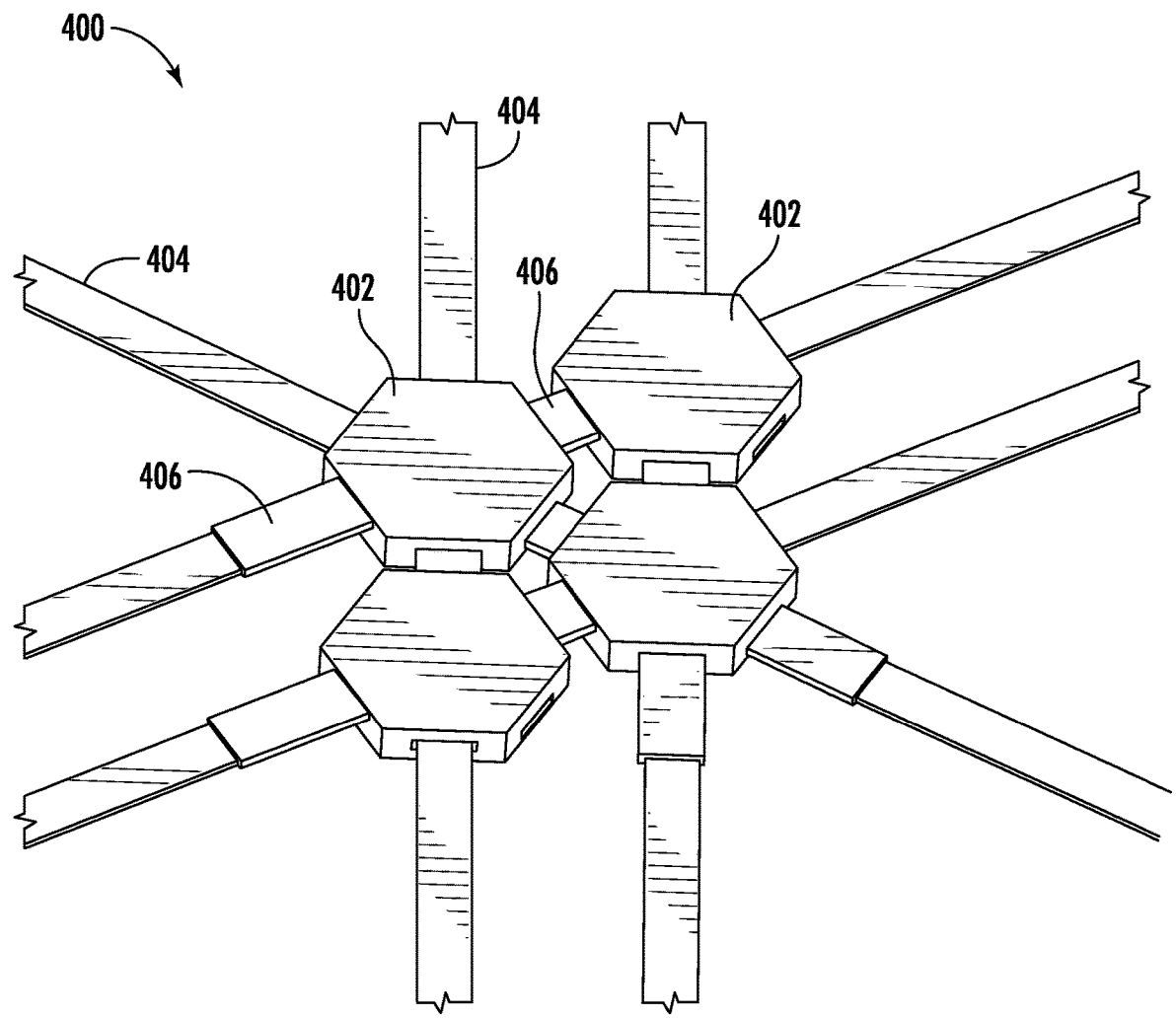
FIG. 17 is a perspective view illustration of at least a portion of a mesh formed from four support members (each hexagonal in shape) having spacer members therebetween according to one embodiment, with five tensile members extending through passages defined in various spacer members and hexagonal support members.

FIG. 17 is a perspective view illustration of at least a portion of a mesh 400 formed from four support members 402 (each being hexagonal in shape) having spacer members 406 therebetween according to one embodiment, with five tensile members 404 extending through passages defined in various spacer members 406 and support members 402. Although four identical support members 402 are shown and each has a hexagonal shape, it is to be appreciated that any suitable number, shape, and configuration of support members 402, spacer members 406, and tensile member 404 may be used to provide a mesh of a desirable size and conformation. In certain embodiments, the tensile members 404 may comprise five limitedly flexible (or limitedly elastic) bands.

Figure 18:
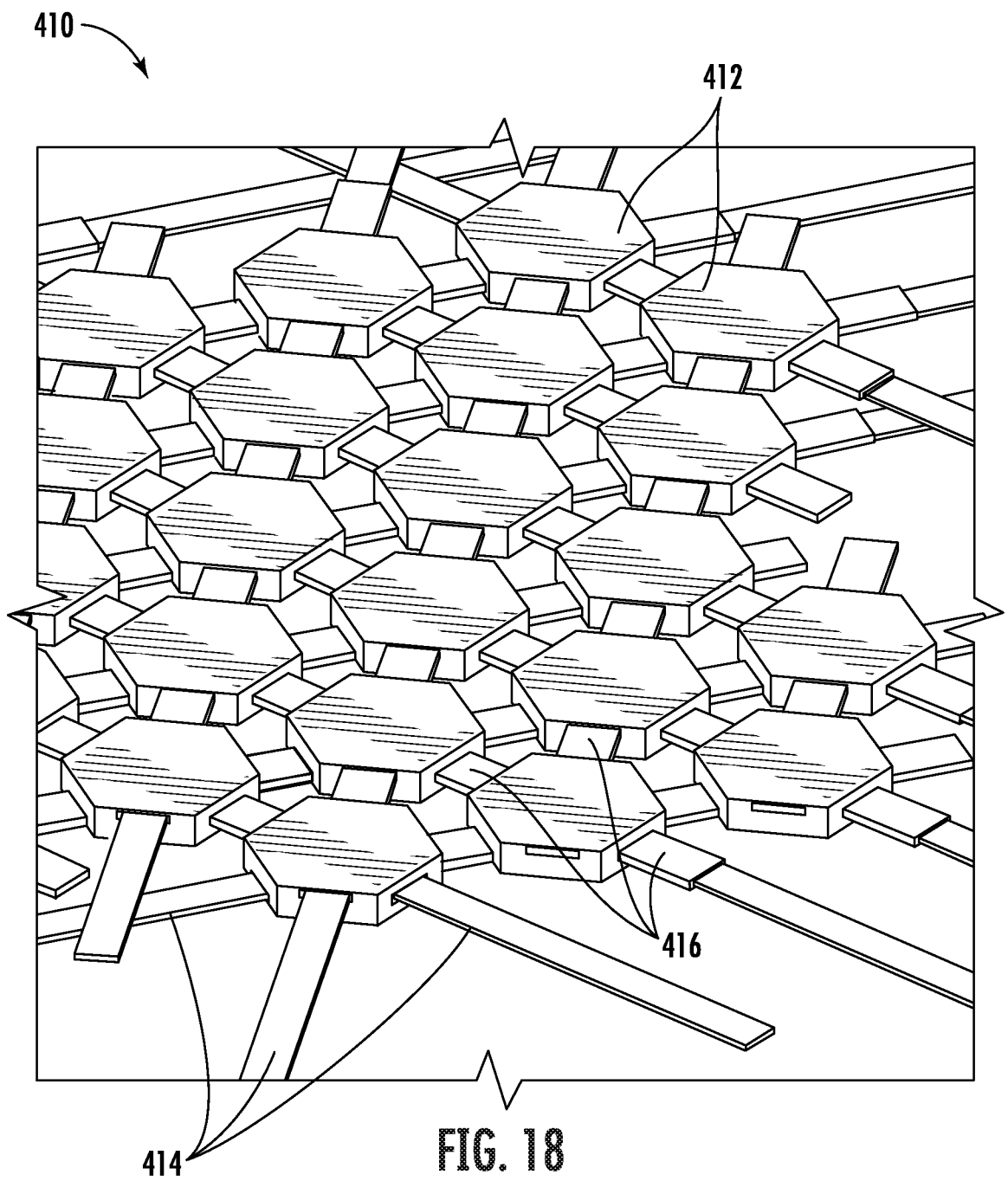
FIG. 18 is a perspective view of a mesh formed from more than twenty hexagonal support members having spacer members arranged therebetween, with tensile members arranged through the support members and spacer members.
Figure 19:
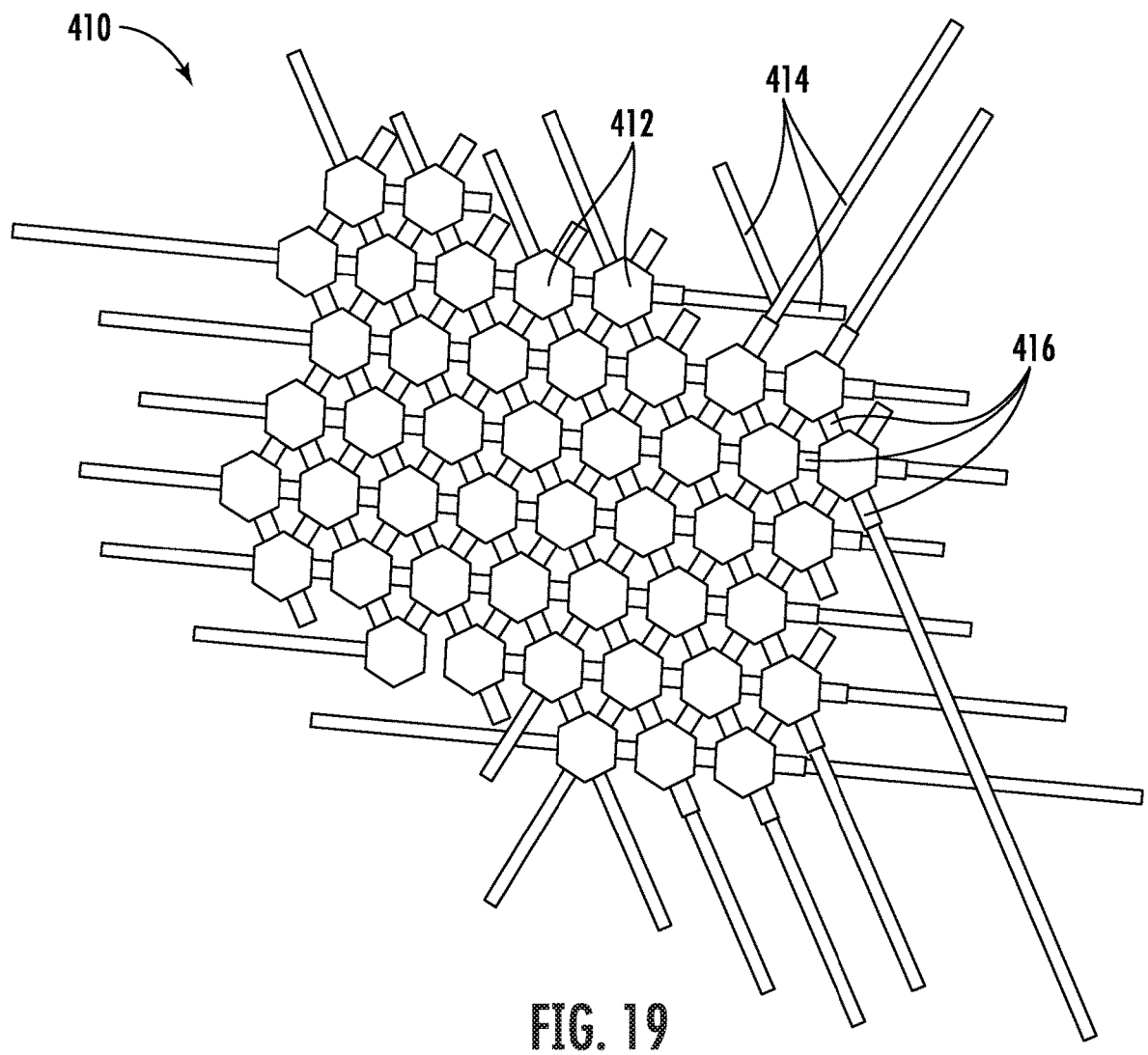
FIG. 19 is a top plan view of a the mesh of FIG. 18.

FIG. 18 is a perspective view of a mesh 410 formed from more than twenty support members 412 (each having a hexagonal shape), numerous spacer members 416 interspersed among the support members 412, and multiple tensile members 414 extending in different directions and passing through passages defined in the support members 412 and tensile members 414. In certain embodiments, portions of spacer members 416 (with tensile members 414 extending through passages defined therein) may be received within passages of support members 412. FIG. 19 is a top plan view of the mesh 410 of FIG. 18, depicting numerous support members 412, spacer members 416, and tensile members 414.

Figure 20:
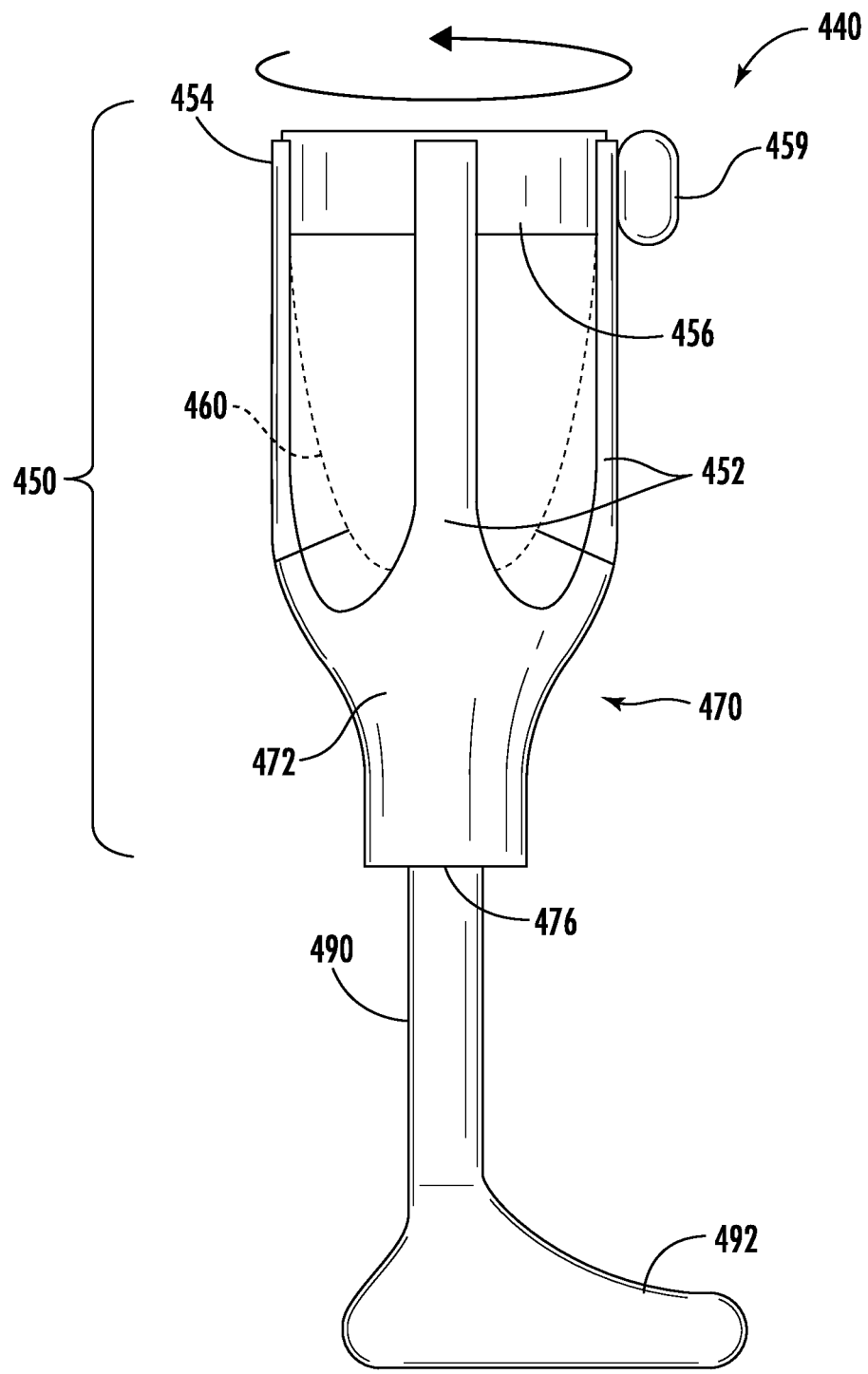
FIG. 20 is a side elevational view of a lower limb prosthesis including a transtibial socket according to one embodiment.

FIG. 20 is a side elevational view of a lower limb prosthesis 440 including a transtibial socket 450 according to one embodiment. In addition to the transtibial socket 450, the lower limb prosthesis 440 includes a foot portion 492 and a lower leg shaft 490 that is received by a receptacle 476 forming a strut/shaft interface of the transtibial socket 450. The receptacle 476 is provided below a tapered outer surface 472 of a base 470 of the transtibial socket 450. The transtibial socket 450 includes struts 452 of rigid material that extend upward from the base 470 toward upper ends 454 that are coupled to a ring-shaped upper transverse member 456 embodied in an adjustable ladder/latch assembly that enables an upper or proximal end of the transtibial socket 450 to be radially adjusted around a residual limb of a user. An adjustment mechanism 459 may be provided to alter a diameter of the upper transverse member 456. A mesh 460 (e.g., including support members, tensile members, optionally in combination with spacer members) as described previously herein is suspended from the upper transverse member 456 and extends into a cavity formed between the struts 452. In certain embodiments, tensile members of the mesh 460 cooperate with the struts 452, such as by being threaded through holes, grommets, or other guiding structures associated with the struts 452. Tensioning members (not shown) may be intermediately arranged between tensile members of the mesh 460 and a tensioning mechanism (not shown) to enable a user to adjust contact pressure (e.g., tightness) of the mesh 460 around a residual limb of the user.

FIG. 21A is a perspective view of a transtibial socket 500 according to one embodiment with variable length strut sections. Multiple (e.g., four) strut bodies 502 and associated variable length strut sections 503 extend upwardly and outwardly from a base 520. Each variable length strut section 503 extends downward from a lower end 507 of a strut body 502. The base 520 includes a tapered outer wall 522 that extends from an upper end 521 to terminate at a lower receptacle 426 serving as a strut/shaft interface to enable coupling with a lower leg shaft (not shown). Each variable length strut section 503 may include metal members that may be repositioned (e.g., lengthened or shortened) with mechanical interfaces 511A such as hex nuts, cotter pins, or the like. A mesh 510 is provided between the struts 502, with the mesh 520 including support members 512 (e.g., of a hexagonal shape) connected with tensile members 514. Portions of the tensile members 514 extending beyond the mesh 510 may serve as tensioning members (e.g., polymer coated steel wires) that are coupled with one or more adjustable tensioning apparatuses 509A, 509B (e.g., arranged proximate to upper ends 504 of the struts 502) to permit radial contraction of the mesh 512 by a user.

FIG. 21B is a side elevational view of one strut body 502 and variable length strut section 503 of the transtibial socket 500 of FIG. 21A. As shown, the variable length strut section 503 may include portions extending upward through a first interface 513A into a lower end 507 of the strut body, and may include portions extending downward through a second interface 513B into a base (not shown). In certain embodiments, each variable length strut section 503 may including one or more telescoping or nested tubular sections to permit aggregate length of a strut to be adjusted to accommodate users and residual limbs of differing sizes (e.g., lengths).

Figure 22:
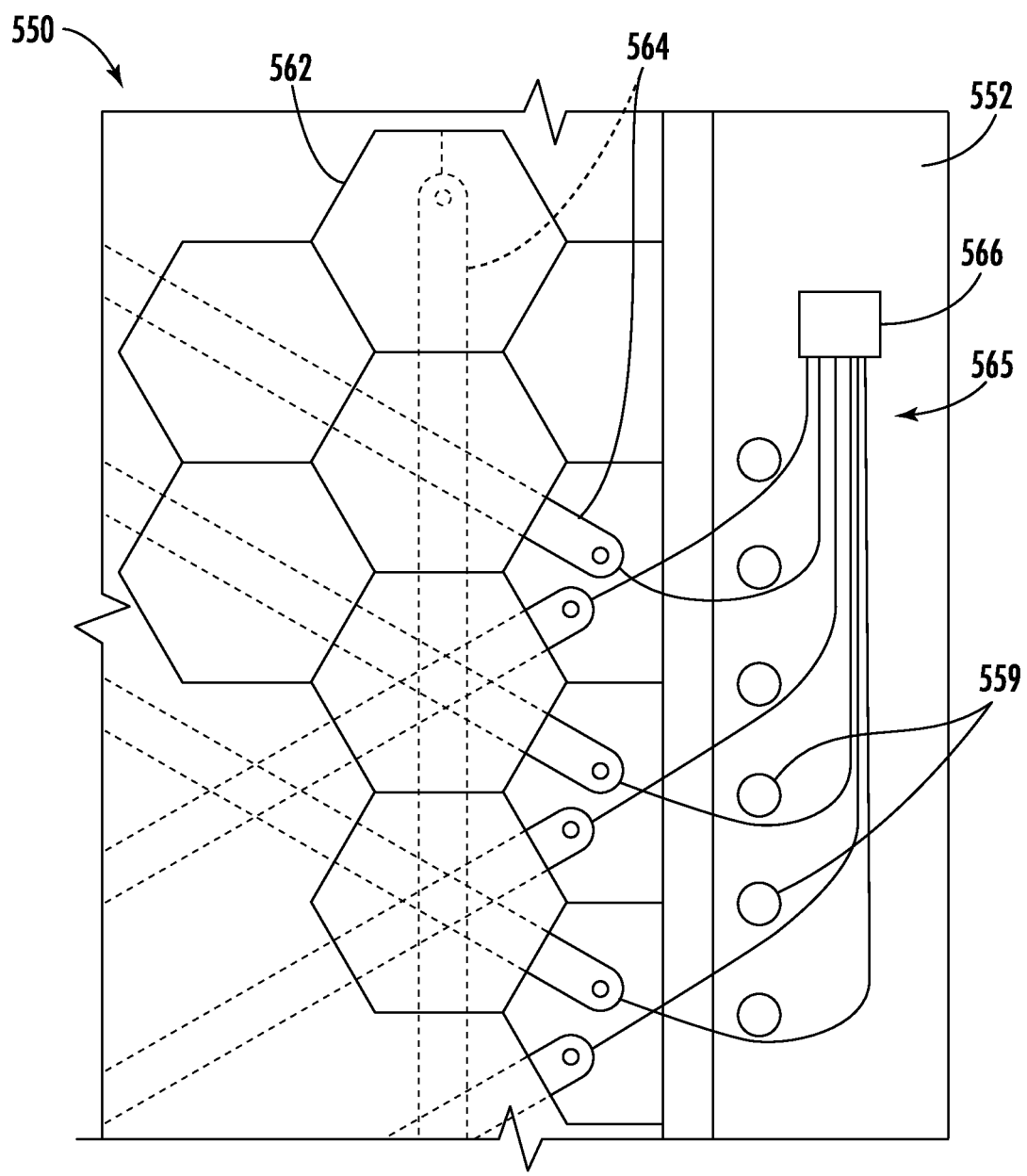
FIG. 22 is a side elevational view of a transtibial socket according to one embodiment, showing tensioning members intermediately arranged between tensile members (e.g., bands) of a mesh and an adjustable tensioning apparatus.

FIG. 22 illustrates a portion of a transtibial socket 550 according to one embodiment, showing tensioning members 565 (e.g., coated wires) intermediately arranged between tensile members 564 of a mesh and an adjustable tensioning apparatus 566 (e.g., a rotary BOA connector, such as described in U.S. Pat. No. 6,289,558 assigned to BOA Technology, Inc.) associated with a carbon fiber strut 552. The strut 55 includes guide members 559 (e.g., loops, holes, or the like) to guide the tensioning members 565 toward the adjustable tensioning apparatus 566. The tensile members 564 extend in different directions through numerous support members 562 each having a hexagonal shape. Upon pulling of the tensioning members 565 and maintenance of tension using the adjustable tensioning apparatus 566, a mesh incorporating the support members 562 and the tensile members 564 may be contracted around a residual limb of a user.

Figure 23:
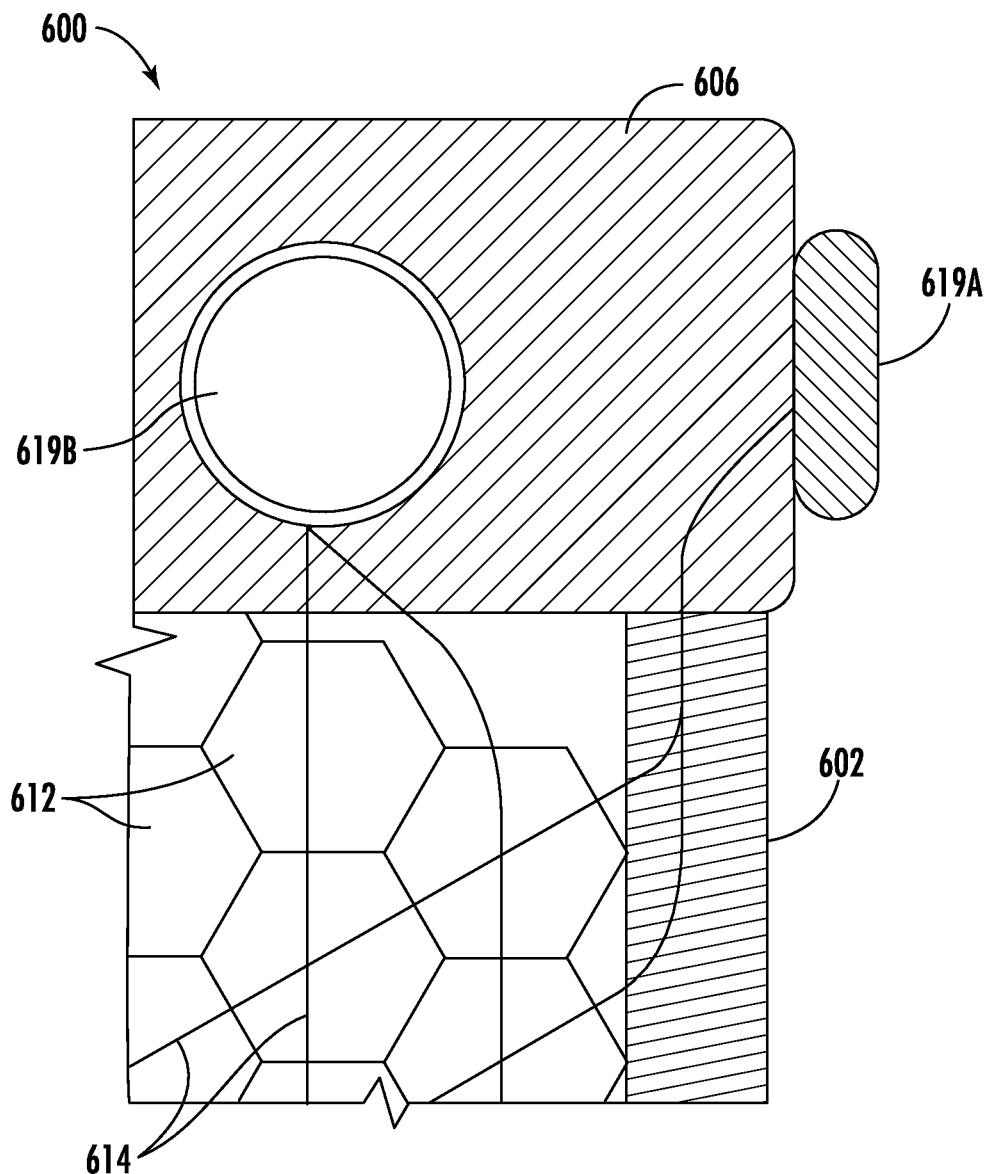
FIG. 23 is a side elevational view of a portion of a transtibial socket according to one embodiment, showing first and second adjustable tensioning apparatuses (e.g., rotary BOA connectors) associated with a top band extending between struts.

FIG. 23 is a side elevational view of an upper portion of a transtibial socket 600 according to one embodiment, showing first and second adjustable tensioning apparatuses 619A, 619B (e.g., rotary BOA connectors) associated with a transverse member 606 (e.g., top band) extending between struts 602, wherein one tensioning apparatus 619A may be used to adjust certain tensioning members 614 and associated tensile members in one direction (e.g., vertical) and another tensioning apparatus may be used to adjust certain tensioning members 614 and associated tensile members in another direction (e.g., diagonal).

Figure 24:
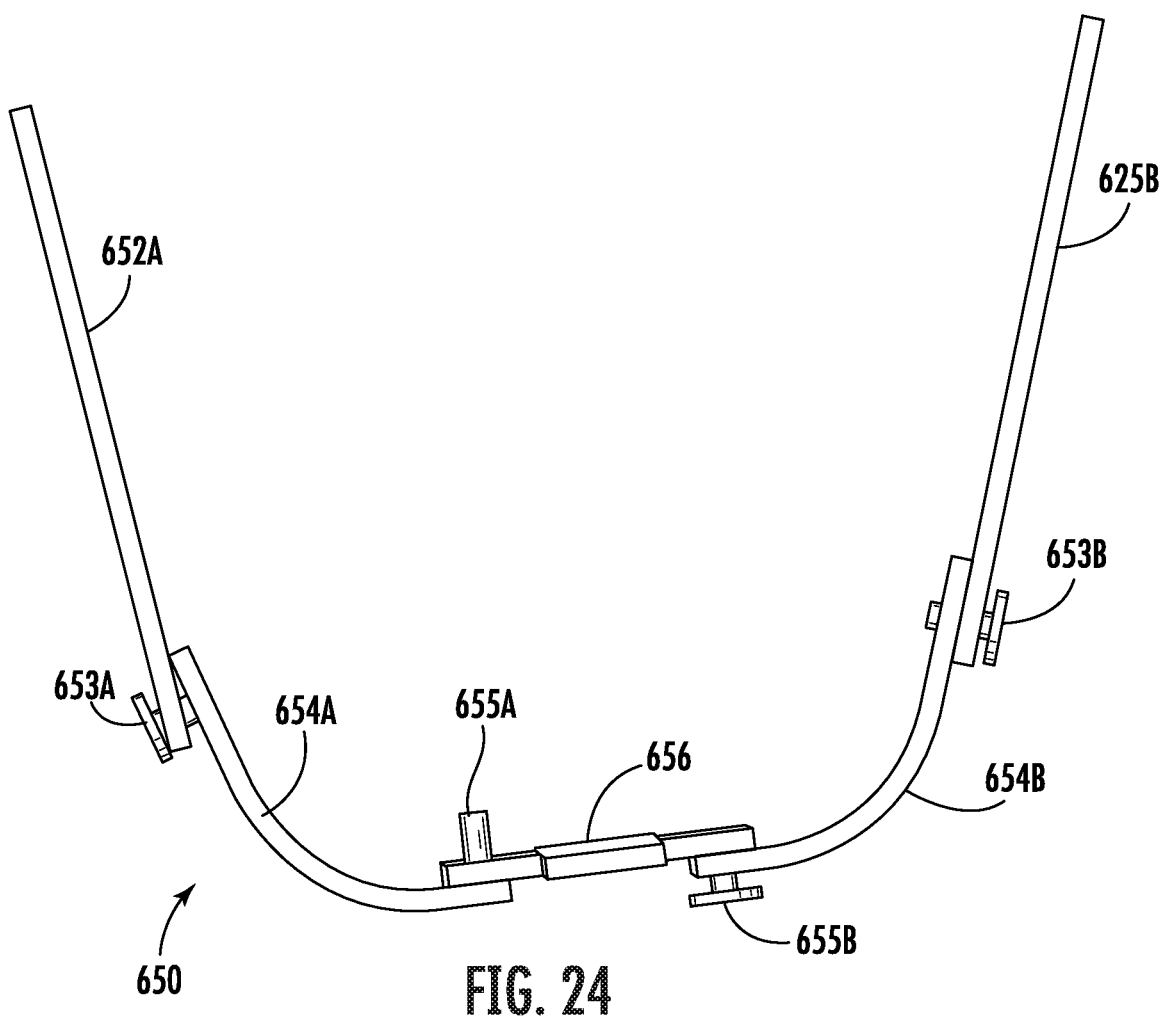
FIG. 24 is a side elevational view of an adjustable rigid structure, showing two (e.g., of four) struts and a base member, wherein the struts may be adjusted in height and in lateral spacing using fasteners (e.g., screws).

FIG. 24 is a side view of an adjustable rigid structure 650, showing two (of four) struts 652A, 652B, a base member 656, and curved coupling members 654A, 654B extending between the base member 656 and the struts 652A, 652B. The struts 652A, 652B may be adjusted in height and in lateral spacing using fasteners 653A, 655A (e.g., screws) in combination with slots or periodically spaced mounting holes associated with the struts 652A, 652B and the curved coupling members 654A, 654B. The base member 656 may serve as a strut/shaft interface.

Figure 25A:
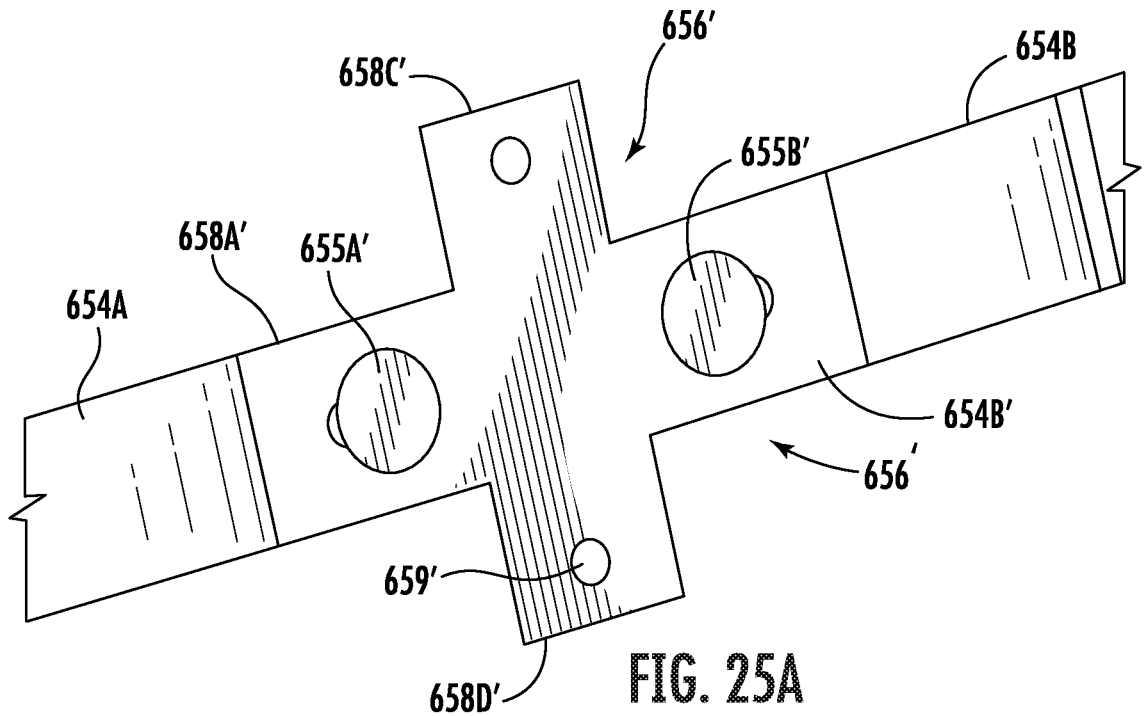
FIGS. 25A and 25B provide top and bottom plan views, respectively, of a modified base member and portions of curved coupling members similar to the corresponding members shown in FIG. 24.
Figure 25B:
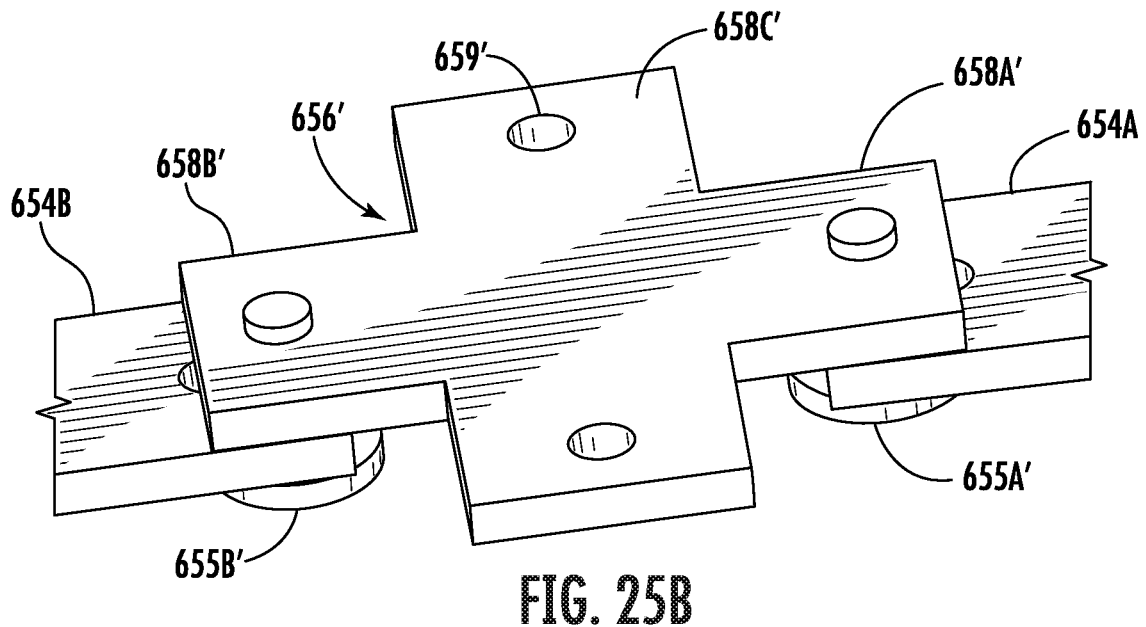

FIGS. 25A and 25B provide top and bottom plan views, respectively, of a modified base member 656' and portions of curved coupling members 654A, 654B similar to the corresponding members shown in FIG. 24. The base member 656' includes first through fourth tab portions 658A'-658D' each arranged ninety degrees apart from one another, and each defining a hole 659' for receiving a fastener (e.g., 655A', 655B'). In certain embodiments, periodically spaced holes or slots may be provided in the curved coupling members 654A, 654B for receiving the fasteners 655A', 655B' therethrough to promote width adjustability. In certain embodiments, the base member 656' and curved coupling members 654A, 654B may be fabricated of carbon fiber, metal, composites, or polymeric material.

Figure 26:
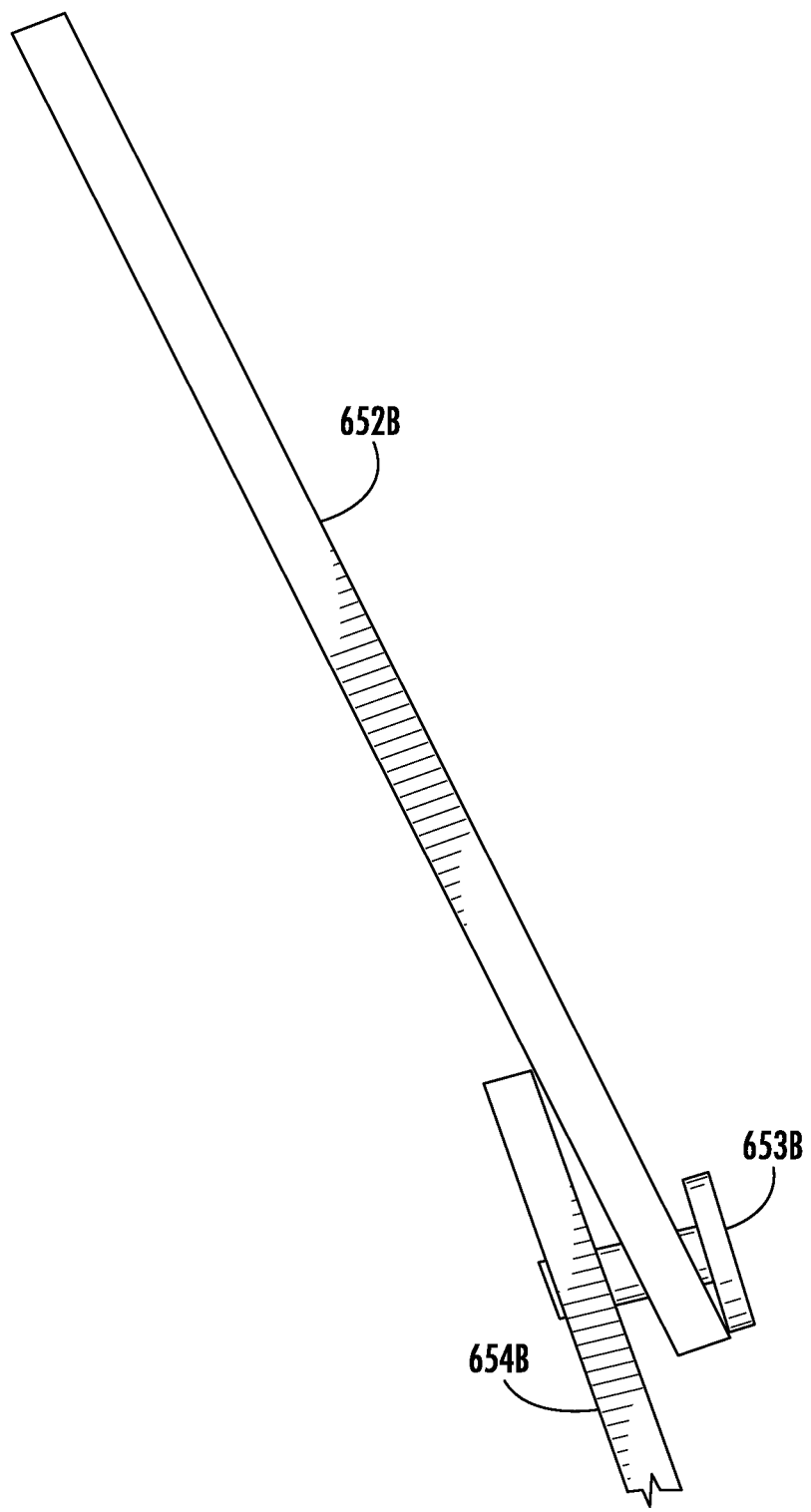
FIG. 26 provides a magnified view of one strut, one fastener, and one curved coupling member shown in FIG. 24.

FIG. 26 provides a magnified view of one strut 652, one fastener 653B, and one curved coupling member 654B shown in FIG. 24.

Figure 27C:
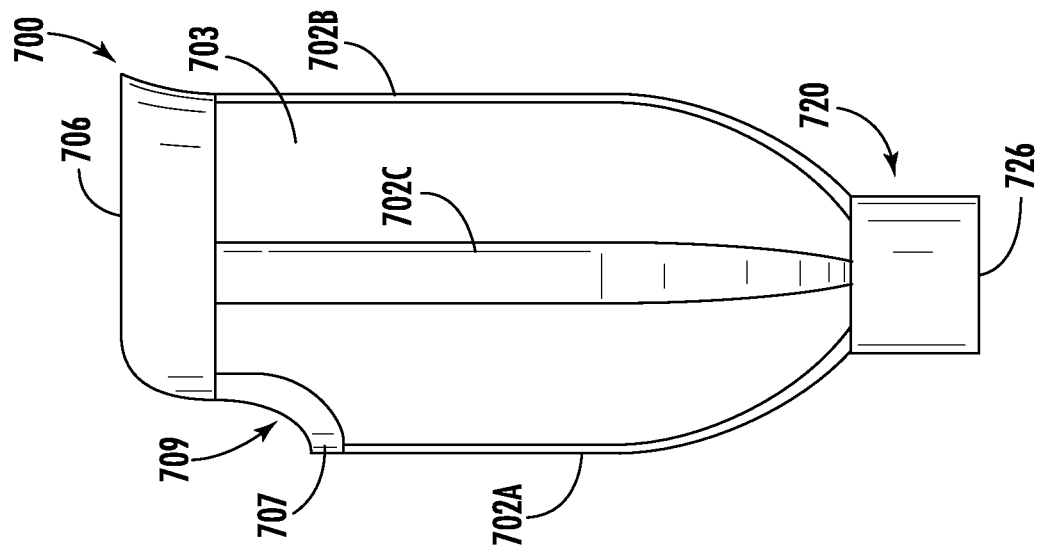
FIG. 27C is a side elevational view of the rigid support structure of FIGS. 27A and 27B.
Figure 27B:
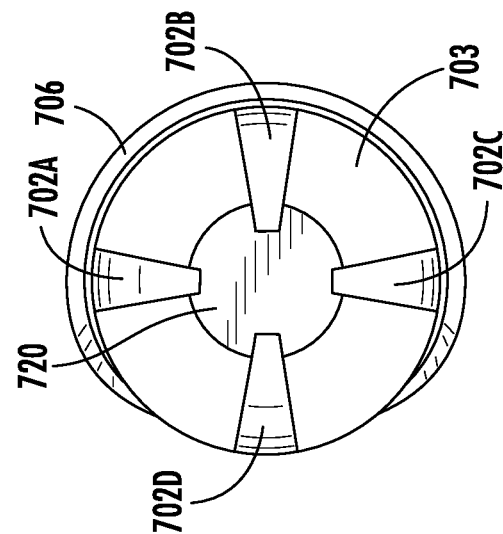
FIG. 27B is a top plan view of the rigid support structure of FIG. 27A.
Figure 27A:
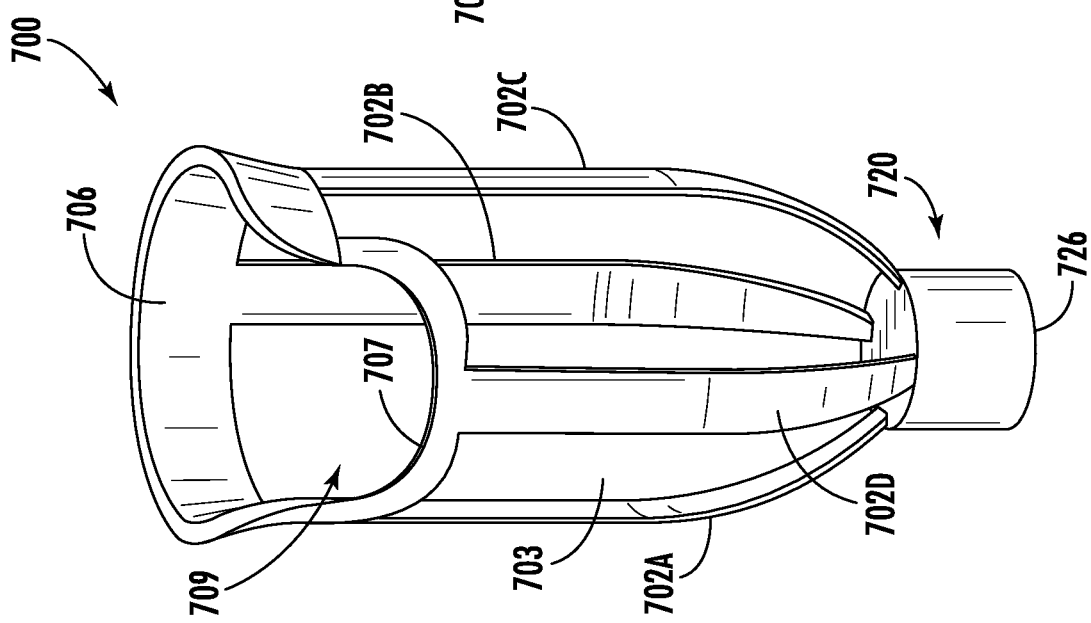
FIG. 27A is a perspective view illustration of a rigid support structure configured to receive a mesh of a transtibial socket according to one embodiment, with the rigid support structure including a strut/shaft interface, four struts, and an upper ring-like structure extending between the struts.

FIGS. 27A-27C illustrate a rigid support structure 700 configured to receive a mesh of a transtibial socket according to one embodiment. FIG. 27A is a perspective view illustration of the rigid support structure 700, while FIGS. 27B and 27C provide top plan and side elevational views thereof, respectively. The rigid support structure 700 includes a base 720 having a receptacle 726 serving as strut/shaft interface, with four struts 702A-702D extending outward and upward from the base 720, and a transverse member 706 embodied in an upper ring-like structure extending between the struts 702A-702D. A cavity 703 is provided between the struts 702A-702D. A downwardly tipped portion 707 of the transverse member 706 forms a cavity 709 that may be suitable for enabling flexure of a user's joint (e.g., knee) in certain embodiments. One strut 702D terminating at the downwardly tipped portion 707 of the transverse member 706 is shorter than the remaining struts 702A-702C.

Figure 28:
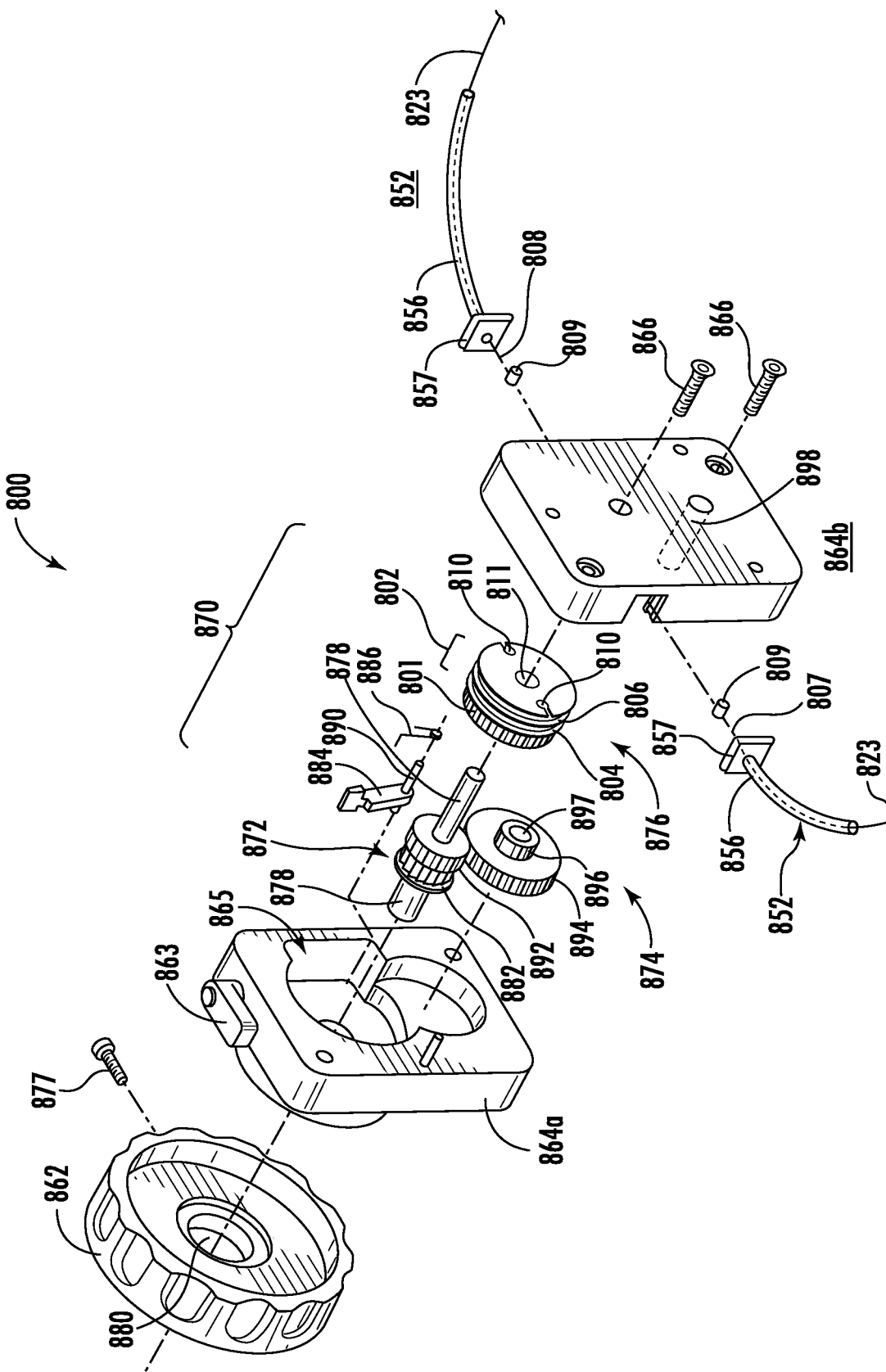
FIG. 28 is an exploded view of a conventional rotary adjustable tensioning apparatus that may be used with transtibial sockets according to various embodiments herein.

FIG. 28 is an exploded perspective view (excerpted from FIG. 8 of U.S. Pat. No. 6,289,558 assigned to BOA Technology, Inc.) of various components of a conventional rotary adjustable tensioning apparatus 800 that may be used to permit adjustment of tension applied to the mesh of a transtibial socket according to one or more embodiments disclosed herein. A housing consists of a pair of interlocking halves 864a, 864b that are mated to each other using fasteners 866, such as screws. The interlocking halves 864a, 864b of the housing enclose a gear mechanism 870 that rotatably fits within cavities 865 defined in inner surfaces of the interlocking halves 864a, 864b. The gear mechanism 870 includes first, second, and third gear wheels 872, 874, 876, respectively, that rotatably engage with each other when the tightening mechanism 800 is assembled.

The first gear wheel 872 includes a shaft 878 about which the first gear wheel 872 rotates. A first portion of the shaft 878 extends through an aperture in the first housing half 864a, and a second portion of the shaft 878 extends through an aperture in the second housing half 64b. A knob 862 mounts to the shaft 878 through a mounting hole 880, and a mounting pin 877 removably secures the knob 862 to the shaft 878. When the tightening mechanism 800 is assembled, rotation of the knob 862 causes the first gear wheel 872 to also rotate, effectuating actuation of the gear mechanism 870. Actuation of a release mechanism 863 permits release of the tightening mechanism 800.

The first gear wheel 872 may also include a ratchet section having a plurality of sloped teeth positioned circumferentially around the axis of the first gear wheel 72, and configured to mate with a pawl 884 to prevent undesired backward rotation of the first gear wheel 872. Toward this end, a biasing member 886 couples to a peg 890 that extends from the pawl 884, with the biasing member 886 serving to bias the pawl 884 against the ratchet teeth when the gear mechanism 870 is assembled. The third gear wheel 872 also includes a gear section 892 having a series of gear teeth that extend around the periphery of the third gear wheel 872.

The second gear wheel 874 includes a first gear section 894 and a stepped second gear section 896 having a diameter smaller than the first gear section 894 on a common axis of rotation. The first gear section 894 has gear teeth that are configured to mesh with the gear section 892 of the first gear wheel 872. An aperture 897 extends centrally through the second gear wheel 874, with the aperture 897 being sized to rotatably receive a post 898 that extends from the housing half 864*b*. The second gear wheel 874 rotates about the post 898 during actuation of the assembled gear mechanism 870.

Rotation of the third gear wheel 806 causes the ends 807 and 808 of the tensioning member 823 to wind around the grooves 804 and 806, respectively, and thereby pull the length of the tensioning member 823 into the tightening mechanism 825 and place the tensioning member 823 in tension. Ends 807, 808 of the tensioning member 823 wind around the spool section 802 at an equal rate so that tension is evenly applied to both ends of the tensioning member 823. The third gear wheel 806 includes a central aperture 811 sized to rotatably receive the shaft 878 on the first gear wheel 872. The third gear wheel 876 rotates about the shaft 878 during actuation of the gear mechanism 870. The third gear wheel 876 includes a gear section 801 that is configured to mesh with the second gear section 896 of the second gear wheel 874. The third gear wheel 876 also includes a spool section 802 comprising grooves 804, 806 that extend around the periphery of the third gear wheel 876. The grooves 804, 806 are sized to receive opposite ends of the tensioning member 823 in a winding fashion during actuation of the gear mechanism 825.

The ends 807 and 808 of the tensioning members 823 are each provided with anchors 809 that mate with seating holes 810 in a press fit fashion. The seating holes 810 are diametrically positioned on the third gear wheel 876. When the anchors 809 are mated with the seating holes 810, the ends 807, 808 of the tensioning members 823 are separately positioned within the grooves 804 and 806, respectively. Guide members 852 (e.g., tubes) may surround portions of the tensioning members 823. The coupling mounts 857 fit into a corresponding aperture in the housing half 864*b* to maintain the distal ends 856 of the guide member 850 in a fixed position relative to the tightening mechanism 800.

An example of producing a transtibial socket according to one embodiment follows.

In one example, hexagonal support members were produced by pouring an air cured hard resin in a silicon gang-style mold with fiberboard inserts, producing ten hexagons with three levels of radially distributed, rectangular paths passing symmetrically through each of the six edges. These hexagonal support members were linked together into the mesh by first connecting them together with semi-flexible hollow spacers of HPDE. Through each pathway, a tensile member embodied in a flat, limitedly elastic band was passed to produce the final mesh. The ends of these bands were connected to a vinyl coated steel wire, allowing them to integrate into a BOA constrictive system (a rotary adjustable tensioning apparatus as described in connection with FIG. 28). A carbon fiber structure of struts, designed to integrate distally with a common lower leg shaft, was produced using generalized geometry of transtibial residual limbs from three-dimensional scans. Tensioning members (e.g., coated wires coupled with the tensile members) from the mesh element were passed around titanium guides on the carbon fiber structure, and threaded through pathways leading to a BOA constrictor unit, allowing for the mesh to be constricted radially by the user. The proximal end of the structure utilized an adjustable constrictive ladder/latch unit to adjust to the radius around the limb. Semi-flexible tensile members within the mesh in combination with the hexagonal geometry of the support members allowed for contraction of the mesh, while retaining rigidity to resist vertical strain and rotational torque that would otherwise act to impede proper force translation when in use.

Those skilled in the art will recognize improvements and modifications to the preferred embodiments of the present disclosure. All such improvements and modifications are considered within the scope of the concepts disclosed herein and the claims that follow.

What is claimed is:

1. A transtibial socket comprising:
   a mesh configured to receive a residual limb of an amputee-user, the mesh comprising a plurality of support members, a plurality of tensile members, and a plurality of spacer members interspersed among the plurality of support members, wherein each support member of the plurality of support members includes a plurality of passages arranged in different directions, and each tensile member of the plurality of tensile members extends through at least one respective spacer member of the plurality of spacer members and extends through one passage of each of multiple respective support members of the plurality of support members, with each tensile member extending through a different combination of support members;
   a plurality of struts positioned around an interior space of the transtibial socket that is configured to receive the mesh, wherein the plurality of struts comprises at least three struts and includes a distal end configured to integrate with a lower leg shaft; and
   a tensioning member coupled with the plurality of tensile members, and extending through or past guides defined in the plurality of struts to an adjustable tensioning apparatus, whereby manipulation of the adjustable tensioning apparatus is configured to selectively tension the tensioning member to allow the mesh to be constricted radially by the amputee-user.

2. The transtibial socket of claim 1, wherein:
   each support member of the plurality of support members includes a plurality of passages; and
   for each support member, different tensile members of the plurality of tensile members extend through different passages of the plurality of passages.

3. The transtibial socket of claim 1, wherein each strut of the plurality of struts comprises an adjustable length, and the transtibial socket further comprises an adjustable constrictive unit enabling a proximal end of the transtibial socket to be radially adjusted around the residual limb of the amputee-user.

4. The transtibial socket of claim 1, wherein for each support member of the plurality of support members, the plurality of passages includes first, second, and third passages each oriented 120 degrees relative to one another, and the first, second, and third passages are non-coplanar.

5. A transtibial socket comprising:
   a mesh configured to receive a residual limb of an amputee-user, the mesh comprising a plurality of support members and a plurality of tensile members, wherein each support member of the plurality of support members includes a plurality of passages arranged in different directions, and each tensile member of the plurality of tensile members extends through one passage of each of multiple respective support members of the plurality of support members, with each tensile member extending through a different combination of support members;

a plurality of struts positioned around an interior space of the transtibial socket that is configured to receive the mesh, wherein the plurality of struts comprises at least three struts and includes a distal end configured to integrate with a lower leg shaft; and a tensioning member coupled with the plurality of tensile members and extending through or past guides defined in the plurality of struts to an adjustable tensioning apparatus, whereby manipulation of the adjustable tensioning apparatus is configured to selectively tension the tensioning member to allow the mesh to be constricted radially by the amputee-user.

6. The transtibial socket of claim 5, further comprising a plurality of spacer members, wherein each spacer member of the plurality of spacer members is respectively arranged between a different pair of the support members of the plurality of support members.

7. The transtibial socket of claim 6, wherein each spacer member of the plurality of spacer members comprises a width, and a width of each spacer member is less than a width of each support member.

8. The transtibial socket of claim 7, wherein each support member of the plurality of support members comprises a support member thickness, and a thickness of each spacer member of the plurality of spacer members is less than the support member thickness.

9. The transtibial socket of claim 5, wherein each support member of the plurality of support members comprises a hexagonal support member.

10. The transtibial socket of claim 5, wherein each support member of the plurality of support members comprises a rounded or non-polygonal shape.

11. The transtibial socket of claim 5, wherein for each support member, different tensile members of the plurality of tensile members extend through different passages of the plurality of passages.

12. The transtibial socket of claim 11, wherein for each support member, the plurality of passages includes first, second, and third passages each oriented 120 degrees relative to one another.

13. The transtibial socket of claim 12, wherein for each support member, the first, second, and third passages are non-coplanar.

14. The transtibial socket of claim 12, wherein for each support member, the first second, and third passages each have a rectangular cross-sectional shape.

15. The transtibial socket of claim 5, wherein each strut of the plurality of struts comprises an adjustable length.

16. The transtibial socket of claim 5, wherein the tensioning member comprises a polymer coated wire.

17. The transtibial socket of claim 5, wherein the adjustable tensioning apparatus comprises a manually operable rotary tensioning apparatus.

18. The transtibial socket of claim 5, further comprising an adjustable constrictive unit enabling a proximal end of the transtibial socket to be radially adjusted around the residual limb of the amputee-user.

19. The transtibial socket of claim 5, wherein each tensile member of the plurality of tensile members comprises an elastic band with a limited degree of stretchability to promote shock absorption.

20. A prosthetic device comprising the transtibial socket according to claim 5.

* * * * *